(12) United States Patent
Karimi et al.

(10) Patent No.: US 9,804,105 B2
(45) Date of Patent: Oct. 31, 2017

(54) SYSTEMS AND METHODS FOR DETERMINING WATER-CUT OF A FLUID MIXTURE

(71) Applicants: Saudi Arabian Oil Company, Dhahran (SA); King Abdullah University of Science and Technology, Thuwal (SA)

(72) Inventors: Muhammad Akram Karimi, Thuwal (SA); Atif Shamim, Thuwal (SA); Muhammad Arsalan, Dhahran (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 227 days.

(21) Appl. No.: 14/838,735

(22) Filed: Aug. 28, 2015

(65) Prior Publication Data

US 2017/0059492 A1 Mar. 2, 2017

(51) Int. Cl.
*G01N 22/04* (2006.01)
*G01N 33/28* (2006.01)

(52) U.S. Cl.
CPC ......... *G01N 22/04* (2013.01); *G01N 33/2823* (2013.01)

(58) Field of Classification Search
CPC ........................... G01N 22/04; G01N 33/2823
(Continued)

(56) References Cited

U.S. PATENT DOCUMENTS 3,498,112 A 3/1970 Howard
3,635,082 A 1/1972 Prellwitz et al.
(Continued)

FOREIGN PATENT DOCUMENTS

CN 2013386555 1/2010
EP 0436286 7/1991
(Continued)

OTHER PUBLICATIONS

Nyfors et al. "Measurement of Mixtures of Oil, Water, and Gas with Microwave Sensors. New Developments and Field Experience of the MFI MultiPhase, and WaterCut Meters of Roxar", SPIE Proceedings | vol. 4129 | Nondestructive Evaluation of Materials by Microwave Techniques, Subsurface Sensing Technologies and Applications II, Jul. 6, 2000.*
McKerricher et al. "Crude Oil Water-Cut Sensing with Disposable Laser Ablated and Inkjet Printed RF Microfluidics", Microwave Symposium (IMS), 2014 IEEE MTT-S International, Jul. 10, 2014.*
(Continued)

*Primary Examiner* — Melissa Koval
*Assistant Examiner* — Courtney McDonnough
(74) *Attorney, Agent, or Firm* — Bracewell LLP; Constance G. Rhebergen; Christopher L. Drymalla

(57) ABSTRACT

Provided in some embodiments are systems and methods for measuring the water content (or water-cut) of a fluid mixture. Provided in some embodiments is a water-cut sensor system that includes a T-resonator, a ground conductor, and a separator. The T-resonator including a feed line, and an open shunt stub conductively coupled to the feed line. The ground conductor including a bottom ground plane opposite the T-resonator and a ground ring conductively coupled to the bottom ground plane, with the feed line overlapping at least a portion of the ground ring. The separator including a dielectric material disposed between the feed line and the portion of the ground ring overlapped by the feed line, and the separator being adapted to electrically isolate the T-resonator from the ground conductor.

23 Claims, 16 Drawing Sheets

(58) Field of Classification Search
USPC .......................................................... 324/634
See application file for complete search history.

(56) References Cited

U.S. PATENT DOCUMENTS

| | | | |
|---|---|---|---|
| 4,499,418 | A | 2/1985 | Helms |
| 4,820,970 | A | 4/1989 | Swanson |
| 4,891,969 | A | 1/1990 | Wayland |
| 4,996,490 | A | 2/1991 | Scott |
| 5,389,883 | A | 2/1995 | Harper |
| 5,485,743 | A | 1/1996 | Taherian et al. |
| 5,864,239 | A | 1/1999 | Adams et al. |
| 5,929,343 | A | 7/1999 | Yamamoto et al. |
| 6,281,801 | B1 | 8/2001 | Cherry et al. |
| 6,441,622 | B1 | 8/2002 | Wrzesinski et al. |
| 6,915,707 | B2 | 6/2005 | Nyfors |
| 7,228,900 | B2 | 6/2007 | Schultz et al. |
| 7,712,381 | B2 | 5/2010 | Allenberg et al. |
| 8,061,186 | B2 | 11/2011 | Gysling |
| 8,225,677 | B2 | 7/2012 | Wang et al. |
| 8,569,296 | B2 | 10/2013 | Liang |
| 8,570,050 | B2 | 10/2013 | Nyfors |
| 8,618,817 | B2 | 12/2013 | Jakoby et al. |
| 8,659,293 | B2 | 2/2014 | Krioutchkov et al. |
| 8,855,947 | B2 | 10/2014 | Sheila-Vadde et al. |
| 9,063,052 | B2 | 6/2015 | Folgeroe et al. |
| 9,541,665 | B2 | 1/2017 | Shanks et al. |
| 2007/0224692 | A1 | 9/2007 | Agar |
| 2012/0035858 | A1 | 2/2012 | Caduff et al. |
| 2013/0033272 | A1 | 2/2013 | Folgeroe et al. |
| 2013/0255821 | A1 | 10/2013 | Roberts |
| 2014/0182737 | A1 | 7/2014 | Jones |
| 2014/0260659 | A1 | 9/2014 | Sheila-Vadde et al. |

FOREIGN PATENT DOCUMENTS

| | | |
|---|---|---|
| GB | 2365978 A | 2/2002 |
| WO | 2012172333 A1 | 12/2012 |
| WO | 2014076506 | 3/2014 |

OTHER PUBLICATIONS

McKerricher G., et al. "Crude oil water-cut sensing with disposable laser ablated and inkjet printed RF microfluidics" Proceedings of the 2014 IEEE MTT-S International Microwave Symposium (IMS2014) Jun. 1, 2014, pp. 1-3.

Nyfors, E., et al. "Measurement of mixtures of oil, water and gas with microwave sensors. New developments and field experience of the MFI MultiPhase, and WaterCut meters of Roxar" Proceedings of SPIE, vol. 4129, Jan. 1, 2000, pp. 12-21.

International Search Report and Written Opinion for International Application No. PCT/US2016/048128; dated Dec. 7, 2016 (pp. 1-15).

Roxar, "Roxar Watercut Meter" available online: http://www2.emersonprocess.com/siteadmincenter/PM%20Roxar%20Documents/Roxar%20Watercut%20meter%20Brochure.pdf, accessed Aug. 27, 2015, pp. 1-16.

AGAR Corporation, "OW-200 Series Oil/Water Meters Liquid/Liquid Concentration" available online: http://www.agarcorp.com/literature/ow200.html, accessed Aug. 27, 2015, pp. 1-4.

Yang, "The Design, Development, and Field Testing of a Water-Cut Meter Based on a Microwave Technique" SPE 20697, Society of Petroleum Engineers Inc. 1990, pp. 775-782.

Wylie, "RF sensor for multiphase flow measurement through an oil pipeline" Institute of Physics Publishing, Meas. Sci. Technol. 17 (2006), pp. 2141-2149.

Nyfors, "Cylindrical Microwave Resonator Sensors for Measuring Materials Under Flow" Report S243, Helsinki University of Technology, Espoo, Finland, May 26, 2000, pp. 1-181.

Dongzhi, "Analysis of Multi-factor Influence on Measurement of Water Content in Crude Oil and Its Prediction Model" Proceedings of the 27th Chinese Control Conference, Jul. 16-18, 2008, pp. 430-435.

Mohamed "Effect of salinity and temperature on water cut determination in oil reservoirs" Journal of Petroleum Science and Engineering 40 (2003), pp. 177-188.

EESiFlo "Water Cut Meter" available online: http://eesiflo.com/water-cut-meter.html, accessed Aug. 27, 2015, pp. 1-3.

Al-Taweel, "Field Testing of Multiphase Meters" SPE 56585, Society of Petroleum Engineers Inc. Oct. 3-6, 1999, pp. 1-16.

* cited by examiner

| $Z_0$ of shunt stub ($\Omega$) | Width of shunt stub (mm) | $\varepsilon_{eff}$ | Fundamental Resonant Frequency "$f_0$" (MHz) | S21 value at $f_0$ (dB) |
|---|---|---|---|---|
| 100 | 1.5 | 1.63 | 229 | -36 |
| 75 | 2.6 | 1.67 | 226 | -37 |
| 50 | 5.1 | 1.73 | 222 | -42 |
| 40 | 7.0 | 1.76 | 220 | -45 |
| 25 | 13.0 | 1.82 | 218 | -47 |

SYSTEMS AND METHODS FOR DETERMINING WATER-CUT OF A FLUID MIXTURE

FIELD OF INVENTION

The present invention relates generally to measurement of fluid content and more particularly to systems and methods for measuring the water content (or water-cut) of a fluid mixture.

BACKGROUND OF THE INVENTION

In some instances oil and gas wells produce oil and gas along with byproducts, such as water. These byproducts can be resident in the formation, or can be introduced into the formation, for example, to assist in producing oil or gas from the well. For example, oil wells are often stimulated using enhanced recovery methods, such as water injection, steam injection, natural gas reinjection and gas lift, to increase rates for recovering oil from oil wells. The water (or other fluids) introduced into the formation can flow into an oil well and mix with the oil. As a result, the oil well may produce a fluid that is a mixture of water and oil. Tracking or otherwise determining the water content in oil, also referred to as "water-cut" can be useful for many reasons. For example, water-cut measurements can be used during production to determine rates for introducing fluids in to a formation or well during the above described enhanced recovery methods, in feasibility analyses of oil wells, in monitoring refining processes (e.g., processes for desalting oil), managing pipeline use, and so forth. Accordingly, many areas, including efficient oil production and refining processes, can benefit from economical systems and methods for obtaining precise measurements of water-cut.

SUMMARY OF THE INVENTION

Applicants have recognized that, due to at least the wide range of uses for water-cut measurements, as well as the variety of environments and locations in which water-cut measurements may be taken, it is desirable to provide economical and robust systems and methods for acquiring precise water-cut measurements. Moreover Applicants have recognized a need for precise on-line/real-time water-cut measurements for continuously monitoring water-cut of fluid flowing through a pipe, such as when an oil and water mixture is flowing through a pipe during oil production, refining processes and/or the like. Applicants have further recognized several shortcomings of existing systems and methods for acquiring precise water-cut measurements. For example, Applicants have recognized that traditional water-cut sensors for acquiring offline water-cut measurements, although sometimes precise, are generally incapable of providing on-line/real-time information, are incapable of sensing water-cut across full water-cut range (e.g., 0% to 100% water concentrations in oil), may be limited to particular uses (e.g., the sensors are only capable for use with a limited range of pipe sizes and/or environments), and/or may not be cost effective. Applicants have also recognized that many water-cut measuring techniques, such as those based on transmissometry, capacitance measurement, Coriolis effect, infrared (IR) spectroscopy, gamma ray spectroscopy and microwave, may each exhibit drawbacks that can make them inadequate for real-time, monitoring of water-cut for fluids during oil production. For example, transmissometry based water-cut sensors can suffer from high signal losses, especially at high water-cut and/or high salinity, which can make them unsuitable for use in high water-cut and/or high salinity conditions. Similarly, capacitive type water-cut sensors may not provide sufficient accuracy for high water-cut (e.g., above about 70%), which can make them unsuitable for use in high water-cut conditions. Coriolis effect based water-cut sensors typically exploit the difference in densities of oil and water, which are not very different. As a result, these types of sensors can suffer from low resolution. IR spectroscopy based water-cut sensors often employ IR sources that are susceptible to harsh-environments. Due to the generally harsh environment of water-cut measurements during oil production, the IR sources may need to be housed in a specialized enclosure, such as a scratch free and hard protective material like sapphire, which can increase complexity and cost, and still may not provide sufficient protection from the harsh environment. Gamma ray spectroscopy based water-cut sensors can present health hazards which can make them difficult to maintain and handle, and limit their use.

With regard to microwave based water-cut sensors, certain microwave based water-cut sensors rely on measuring a phase difference between transmitted and received microwave signals, which can have a direct link with the effective permittivity of the oil and water mixture. Some microwave based water-cut sensors may exhibit high losses and, as a result, may not operate reliably under high water-cut conditions, especially for larger pipe sizes. In some instances, microwave based water-cut sensors for measuring water-cut of fluid flowing through pipes can employ transmit (Tx) and receive (Rx) antennas disposed inside of the pipe, such that the antennas are at least partially immersed in the fluid mixture as it flows through the pipe. The portions of the antennas immersed in the fluid flow can inhibit the fluid flow in the pipe, which can cause an undesirable pressure loss in the fluid flow.

In some instances, microwave based water-cut sensors can employ non-planar microwave resonators. Such resonators can be based upon either quasi cavity resonator ("quasi" in the sense that such cavity resonators have open or partially open ends to have minimum flow hindrance), cylindrical fin resonator (CFR) or terminated transmission lines (twin wire or coaxial). Applicants have recognized that, these types of microwave based water-cut sensors can still suffer from shortcomings. For example, cavity resonators may require complex feeding mechanisms through Tx and Rx antennas, CFRs may be intrusive in nature, and transmission line (TL) based resonators may need to be implemented in a bypass fashion to main flow stream.

Recognizing these and other shortcomings of existing systems, Applicants have developed novel systems and methods for measuring water-cut of a fluid mixture in a pipe (e.g., the water concentration of an oil and water mixture flowing through a cylindrical pipe). For example, described herein are embodiments of microwave resonator based water-cut (WC) sensors, and associated systems and methods. In some embodiments, a WC sensor employs dual ground planes disposed at least partially on opposite sides of a pipe. For example, certain embodiments can include a T-resonator generally located on one side of the pipe and a ground plane generally located on the opposite side of the pipe. Such a WC sensor may be suitable for use with wide range of pipe sizes, such as the various large and small pipes used in oil industry. As further described herein, certain embodiments of a WC sensor may employ the principles of series resonance introduced by a $\lambda/4$ open shunt stub located in the middle of a microstrip line. In certain embodiments, a corresponding WC determination can be based on the measurement of a WC sensor's resonance frequency (e.g., the resonance frequency of a T-resonator of the WC sensor) which can vary with the relative percentage of oil and water due to the difference in their dielectric properties. As described herein, such a WC sensor may provide for non-intrusive, in-situ water-cut sensing over full range of operation (e.g., for sensing water-cut of fluids having 0%-100% volumetric fraction of water in oil).

Provided in some embodiments is a water-cut sensor system that includes a cylindrical pipe, a microwave resonator water-cut sensor, and a measurement system. The cylindrical pipe for routing the flow of a production fluid including a mixture of oil and water. The microwave resonator water-cut sensor including a T-resonator, a ground conductor, and a separator. The T-resonator disposed on a first side of a cylindrical pipe and including: a feed line including a conductive material disposed about a first portion of an external surface of the cylindrical pipe extending in a circumferential direction about the cylindrical pipe; an open shunt stub including a conductive material disposed on a second portion of the external surface of the cylindrical pipe extending in a longitudinal direction along the cylindrical pipe, the open shunt stub being conductively coupled to the feed line; an input terminal located at a first end of the feed line; and an output terminal located at a second end of the feed line. The ground conductor being disposed on a second side of the cylindrical pipe that is opposite the first side. The ground conductor including: a ground plane including a conductive material disposed on a third portion of the external surface of the cylindrical pipe extending in the longitudinal direction along the cylindrical pipe, with the third portion of the external surface of the pipe being opposite the second portion of the external surface of the pipe (such that the open shunt stub is disposed on the first side of the cylindrical pipe and the ground plane is disposed on a second side of the cylindrical pipe that is opposite the first side); and a ground ring including a conductive material disposed on a fourth portion of the external surface of the cylindrical pipe extending in a longitudinal direction. The ground ring being conductively coupled to the ground plane, and the first portion overlapping the fourth portion such that the feed line overlaps the ground ring. The separator including a dielectric material disposed between the feed line and the portion of the ground ring overlapped by the feed line. The separator being adapted to electrically isolate the T-resonator from the ground conductor. The measurement system operable to: introduce, to the feed line of the T-resonator via the input terminal, source signals of different frequencies; sense, from the feed line of the T-resonator via the output terminal, response signals corresponding to the source signals; determine a resonance frequency of the microwave resonator water-cut sensor based at least in part on the source signals and the response signals; and determine a percentage of oil or water in the fluid based at least in part on the resonance frequency of the microwave resonator water-cut sensor.

In certain embodiments, the open shunt stub has a length that is the same or greater than a diameter of the cylindrical pipe. In some embodiments, the open shunt stub has a length that is between three and five times the diameter of the cylindrical pipe. In certain embodiments, the feed line has a length that is the same or greater than a width of the shunt stub. In some embodiments, the ground ring has a width that is the same or greater than a width of the feed line. In certain embodiments, the separator has a width that is the same or greater than a width of the feed line, and a length that is the same or greater than a length of the feed line. In some embodiments, the ground plane has a width determined based on an average of a first width associated with a minimum resonance frequency for oil and a second width associated with a minimum resonance frequency for water.

In certain embodiments, determining a resonance frequency of the microwave resonator water-cut sensor based at least in part on the source signals and the response signals includes determining a frequency corresponding to a low point of a S21 response determined based on the source signals and the response signals. In some embodiments, introducing source signals of one or more frequencies includes conducting a frequency sweep across an operating range for the microwave resonator water-cut sensor.

Provided in some embodiments is a water-cut sensor system that includes a T-resonator, a ground conductor, and a separator. The T-resonator including: a feed line including a conductive material disposed about a first portion of an external surface of a pipe extending in a circumferential direction about the pipe; and an open shunt stub including a conductive material disposed on a second portion of the external surface of the pipe extending in a longitudinal direction along the pipe, the open shunt stub being conductively coupled to the feed line. The ground conductor including: a ground plane including a conductive material disposed on a third portion of the external surface of the cylindrical pipe extending in the longitudinal direction along the cylindrical pipe, where the third portion of the external surface of the pipe is opposite the second portion of the external surface of the pipe; and a ground ring including a conductive material disposed on a fourth portion of the external surface of the cylindrical pipe extending in a longitudinal direction. The ground ring being conductively coupled to the ground plane, and the first portion overlapping the fourth portion such that the feed line overlaps the ground ring. The separator including a dielectric material disposed between the feed line and the portion of the ground ring overlapped by the feed line, and the separator being adapted to electrically isolate the T-resonator from the ground conductor.

In certain embodiments, the open shunt stub has a length that is the same or greater than a diameter of the pipe. In some embodiments, the open shunt stub has a length that is between three and five times the diameter of the pipe. In certain embodiments, the feed line has a length that is the same or greater than a width of the shunt stub. In some embodiments, the ground ring has a width that is the same or greater than a width of the feed line. In certain embodiments, the separator has a width that is the same or greater than a width of the feed line, and a length that is the same or greater than a length of the feed line. In some embodiments, the ground plane has a width determined based on an average of a first width associated with a minimum resonance frequency for oil and a second width associated with a minimum resonance frequency for water.

In certain embodiments, the pipe is a cylindrical pipe, and the T-resonator is disposed on a first side of the pipe, and the ground conductor is disposed on a second side of the pipe that is opposite the first side of the pipe. In some embodiments, the T-resonator includes: an input terminal located at a first end of the feed line, where the input terminal is adapted to receive source signals from an external circuit; and an output terminal located at a second end of the feed line, where the output terminal is adapted to provide for sensing, by an external circuit, of response signals corresponding to the source signals. Further, a resonance frequency of the microwave resonator water-cut sensor is determined based at least in part on the source signals and the response signals, and a water-cut of fluid in the cylindrical pipe is determined based at least in part on the resonance frequency of the microwave resonator water-cut sensor.

In certain embodiments, the system further includes a measurement system adapted to: introduce, to the feed line of the T-resonator, source signals of different frequencies; sense, from the feed line of the T-resonator, response signals corresponding to the source signals; determine a resonance frequency based at least in part on the source signals and the response signals; and determine a water-cut of a fluid in the pipe based at least in part on the resonance frequency of the microwave resonator water-cut sensor. In some embodiments, determining a resonance frequency based at least in part on the source signals and the response signals includes determining a frequency corresponding to a low point of a S21 response determined based on the source signals and the response signals. In certain embodiments, introducing source signals of one or more frequencies includes conducting a frequency sweep across an operating range for the water-cut sensor.

Provided in some embodiments is a method for sensing water-cut of a fluid in a cylindrical pipe. The method including: introducing, to a T-resonator of a water-cut sensor disposed on the cylindrical pipe, source signals of different frequencies; sensing, from the T-resonator of the water-cut sensor, response signals corresponding to the source signals; determining a resonance frequency of the water-cut sensor based at least in part on the source signals and the response signals; and determining a percentage of oil or water in the fluid based at least in part on the resonance frequency of the water-cut sensor.

In certain embodiments, the water-cut sensor includes a T-resonator, a ground conductor, and a separator. The T-resonator including: a feed line including a conductive material disposed about a first portion of an external surface of a pipe extending in a circumferential direction about the pipe; and an open shunt stub including a conductive material disposed on a second portion of the external surface of the pipe extending in a longitudinal direction along the pipe, with the open shunt stub being conductively coupled to the feed line. The ground conductor including: a ground plane including a conductive material disposed on a third portion of the external surface of the cylindrical pipe extending in the longitudinal direction along the cylindrical pipe, wherein the third portion of the external surface of the pipe is opposite the second portion of the external surface of the pipe; and a ground ring including a conductive material disposed on a fourth portion of the external surface of the cylindrical pipe extending in a longitudinal direction. The ground ring being conductively coupled to the ground plane, and the first portion overlapping the fourth portion such that the feed line overlaps the ground ring. The separator including a dielectric material disposed between the feed line and the portion of the ground ring overlapped by the feed line, and the separator being adapted to electrically isolate the T-resonator from the ground conductor.

Provided in some embodiments is a method for manufacturing a water-cut sensor. The method including: disposing a first mask on an external surface of the pipe, with the first mask including a first opening at a first portion of the external surface of the pipe for forming an open shunt stub of a T-resonator; disposing a conductive material into the first opening to form the open shunt stub of the T-resonator on the first portion of the external surface of the pipe; disposing a second mask on the external surface of the pipe, the second mask including a second opening at a second portion of the external surface of the pipe for forming a ground plane of a ground conductor, with the second portion of the external surface being opposite the first portion of the external surface; disposing a conductive material into the second opening to form the ground plane of the ground conductor on the second portion of the external surface of the pipe; disposing a third mask on an external surface of the pipe, with the third mask including a third opening at a third portion of the external surface of the pipe for forming a ground ring of the ground conductor, the third portion extending at least from the ground plane about a circumference of the pipe; disposing a conductive material into the third opening to form the ground ring of the ground conductor on the third portion of the external surface of the pipe, with the ground ring being conductively coupled to the ground plane; disposing a dielectric separator on at least a portion of the ground ring to be overlapped by a feed line of the T-resonator; disposing a fourth mask on an external surface of the pipe, with the fourth mask including a fourth opening at an external surface of the dielectric separator for forming the feed line of the T-resonator; and disposing a conductive material into the fourth opening to form the feed line of the T-resonator on the external surface of the dielectric separator, with the feed line being conductively coupled to the open shunt stub.

Figure 1:
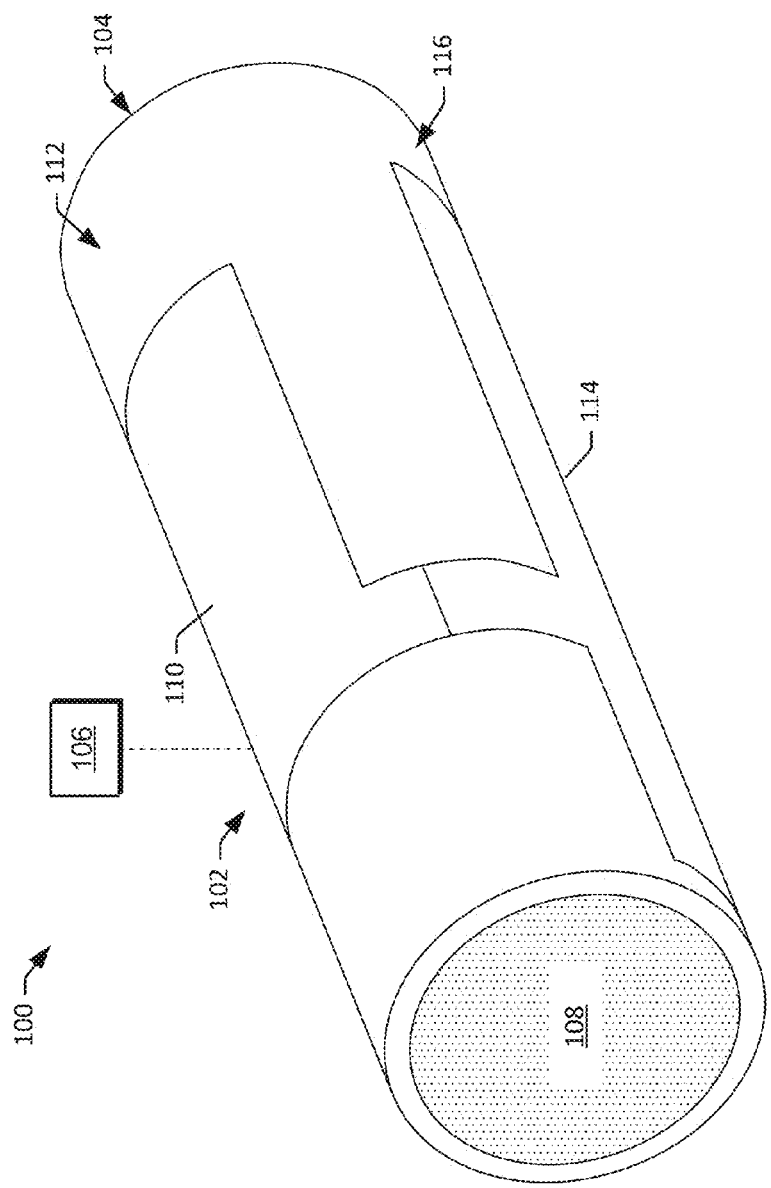
FIG. 1 is a block diagram that illustrates an example water-cut (WC) sensing system in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

The present invention will now be described more fully hereinafter with reference to the accompanying drawings in which example embodiments of the invention are shown. This invention may, however, be embodied in many different forms and should not be construed as limited to the illustrated embodiments set forth herein, rather, these example embodiments are provided so that this disclosure will be thorough and complete, and will fully convey the scope of the invention to those skilled in the art.

Described herein are systems and methods for measuring the water content (or water-cut) of a fluid mixture. For example, certain embodiments are provide for measuring water content in oil (e.g., volumetric fraction of water in oil), also referred to as water-cut (WC). In some embodiments, provided is a microwave resonator based water-cut (WC) sensor, and associated systems and methods. In some embodiments, a WC sensor can provide non-intrusive, in-situ water-cut sensing over full range of operation (e.g., sensing water-cut of fluids having 0%-100% volumetric fraction of water in oil). As described herein, in some embodiments, a WC sensor employs series resonance introduced by a λ/4 open shunt stub located in the middle of a microstrip line. In some embodiments, a WC sensor can include a planar microwave resonator. For example, a WC sensor may include a signal conductor (SC) (e.g., a first plane) disposed at a first/upper/top surface of a cylindrical pipe, and a ground conductor (GC) (e.g., a second plane) disposed at a second/lower/bottom surface of the cylindrical pipe that is opposite the first/upper/top surface of the pipe. In some embodiments, the signal conductor may include a "T-resonator". For example, the signal conductor may include a generally "T" shaped conductive material (e.g., copper) disposed along the length of the first/upper/top surface of the pipe. The ground conductor may include a generally rectangular shaped conductive material (e.g., copper) that is disposed along the length of the second/lower/bottom surface of the pipe and may include a ground ring that wraps around the circumference (e.g., wraps about the diameter) of the pipe and under a feed line of the T-resonator. Further details of embodiments of such a WC sensor system, and relevant concepts behind the embodiments, are discussed in more detail herein.

FIG. 1 is a block diagram that illustrates an example water-cut (WC) sensing system 100 in accordance with one or more embodiments. In some embodiments, the WC sensing system 100 includes a water-cut (WC) sensor 102, a cylindrical pipe 104, and/or a measurement processing system 106. As discussed herein, the water-cut (WC) sensor 102 may be disposed on (or otherwise integrated with) the cylindrical pipe 104. In some embodiments, the WC sensor 102 can include a first/signal conductor (SC) 110 (e.g., a first conductive plane), such as a T-resonator, disposed at a first/upper/top surface 112 of the cylindrical pipe 104, and a ground conductor (GC) 114 (e.g., a second conductive plane) disposed at a second/lower/bottom surface 116 of the cylindrical pipe 104 that is opposite the first/upper/top surface 112 of the pipe 104. That is, the center of the ground conductor 114 may be disposed about 180 degrees about the longitudinal axis of the pipe 104 from the center of the signal conductor 110. In some embodiments, the ground conductor 114 may include a ring portion that extends about the circumference of the pipe 104. Thus, the ground conductor 114 may have a conductive path that wraps completely around the pipe 104. Certain embodiments of a WC sensor system employing a T-resonator, are discussed in more detail herein with regard to at least FIGS. 10A-10E.

In such as configuration, the WC sensing system 100 can be employed to sense a water-cut of a fluid 108 (e.g., a water and oil mixture) (or other substrate) flowing through, or otherwise present in, the pipe 104. For example, the measurement processing system 106 may introduce one or more source signals into the WC sensor 102 and/or sense one or more corresponding response signals from the WC sensor 102, and may analyze the characteristics of the one or more source signals and/or the one or more corresponding response signals to determine a resonance frequency of the WC sensor 102 in the presence of the fluid 108 (e.g., a resonance frequency of the signal conductor 110 (e.g. the T-resonator) with the fluid 108 currently flowing through or otherwise located in the pipe 104 (e.g., the fluid 108 located between the signal conductor 110 and the ground conductor 114), and based on a predetermined correlation between the water-cut of a fluid mixture flowing through the pipe 104 and the resonance frequency of the WC sensor 102, determine the water-cut of the fluid 108. That is, the water-cut of the fluid 108 passing through the pipe 108 can be determined based on the resonance frequency of the WC sensor 102 at or near the time when the fluid 108 passes through the portion of the pipe 104 on which the WC sensor 102 is disposed. As described herein, such a WC sensor 102 may be non-intrusive, may be scaled to a wide variety of pipe sizes, may be implemented using relatively simple and inexpensive manufacturing techniques, and may be able to achieve at least about 0.1% repeatability.

Although certain embodiments are described herein with regard to a T-resonator type signal conductor 110 for the purpose of illustration, embodiments can include any suitable type/shaped signal conductor 110. For example, embodiments can be employed using a ring type signal conductor 110, or other suitable type/shape signal conductor 110, in place of or in conjunction with a T-resonator type signal conductor 110. Embodiments of a WC sensor system employing a ring type signal conductor 110 (e.g., a "ring-resonator" are discussed in more detail herein with regard to at least FIG. 4. Further details of embodiments of such a WC sensor system 100, and relevant concepts behind the embodiments, including certain characteristics of the various elements of embodiments of the WC sensor system 100, such as the shapes, dimensions, placement and/or the like of signal and/or ground conductors, are discussed in more detail herein.

In some embodiments, a microwave resonator of a WC sensor described herein may be characterized in a manner similar to a transmission line (TL), with a fluid present between the signal and ground conductors of the WC sensor being characterized as a substrate of the TL. The characteristic impedance of a transmission line may be the ratio of the voltage and current of a wave travelling along the line. When the wave reaches the end of the line, in general, there can be a reflected wave which travels back along the line in the opposite direction. When this wave reaches the source, it may add to the transmitted wave and the ratio of the voltage and current at the input to the line may no longer be the characteristic impedance. This new ratio is called the input impedance. The input impedance of an infinite line may equal the characteristic impedance since the transmitted wave is never reflected back from the end. It can be shown that an equivalent definition is: the characteristic impedance of a line is that impedance which when terminating an arbitrary length of line at its output will produce an input impedance equal to the characteristic impedance. This is so because there is no reflection on a line terminated in its own characteristic impedance.

A substrate (e.g., with dielectric constant of ($\in_r$) and loss tangent (tan δ)) may define the capacitance (C) and conductance (G) of a transmission line (TL) which affects its characteristic impedance ($Z_0$), as evident from the following equations for characteristic impedance ($Z_0$) (eq. 1), and speed of microwaves passing through it (eq. 2). Characteristic impedance ($Z_0$) for a transmission (TL) may be expressed as follows:

$$Z_O = \sqrt{\frac{R + j\omega L}{G + j\omega C}} \quad (1)$$

where R is the resistance per unit length, considering the two conductors to be in series, L is the inductance per unit length, G is the conductance of the dielectric per unit length, C is the capacitance per unit length, j is the imaginary unit, and ω is the angular frequency. Microwaves may be passed through a dielectric medium by alternate cycles of charging and discharging, such that high storage capacity (e.g., high capacitance or $\in_r$) of the substrate can cause hindrance in changing polarity, thereby causing a reduction in the speed of microwaves, as evidenced by (eq 2). The velocity (v) of a microwave in a dielectric medium can be expressed as follows:

$$v = \frac{c}{\sqrt{\varepsilon_{eff1}}} \quad (2)$$

where c is the speed of light (e.g., about 2.998×10⁸ meters per second (m/s)), and $\in_{eff1}$ is the effective permittivity of the dielectric medium through which the microwave is traveling and depends upon the fringing field pattern defined by the placement of signal and ground conductors. A difference in speed of microwaves can cause a TL of the same physical length to appear electrically different for substrates of different dielectric constants ($\in_r$) (e.g., which may vary from about 2.6 to about 80 for different water-cuts). The microwave resonance phenomenon may be based upon the superposition of two oppositely travelling waves which causes the standing wave pattern to appear at different frequencies, depending upon the speed of microwaves, as provided by equation 2. As such, resonance frequency of a microwave resonator may be correlated with the substrate's dielectric constants ($\in_r$).

In some embodiments, planar microwave resonators can be constructed using different transmission line (TL) modes. For example, resonators can be constructed using a microstrip line mode configuration or a co-planar waveguide (CPW) mode configuration. A microstrip line mode configuration may employ sandwiching of a dielectric medium between a signal conductor and ground conductor. A CPW mode configuration may employ conductors disposed side-by-side on the surface of a dielectric medium. Of these two modes, microstrip line may more sensitive to the change in dielectric properties of the substrate. This sensitivity of microstrip line may be attributable to its sandwiching of a dielectric medium between signal and ground conductors, which can enable electric fields (E fields) and magnetic field (H fields) to penetrate into and through the medium located there between. In contrast, the side by side conductor placement a CPW mode may allow a relatively large proportion of fields to be directed into air adjacent the medium, with less fields penetrating into and through the medium.

Figure 2A:
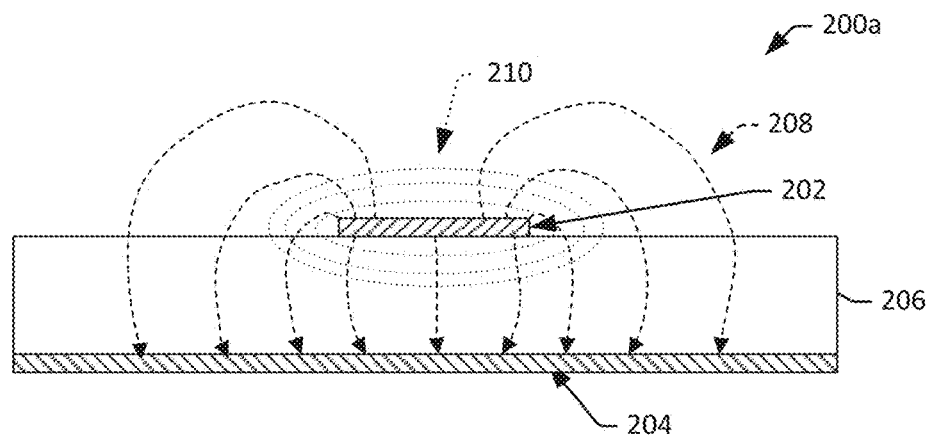
FIGS. 2A and 2B are diagrams that illustrate example microwave resonator systems employing a microstrip line mode and a co-planer waveguide mode, respectively, in accordance with one or more embodiments.
Figure 2B:
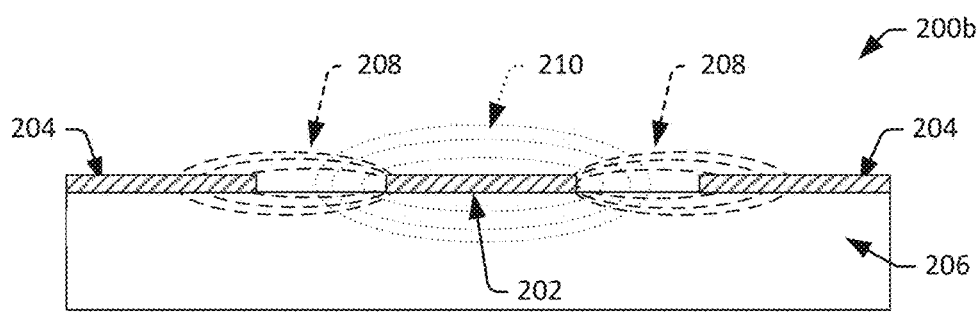

FIGS. 2A and 2B are diagrams that illustrate example microwave resonator systems 200a and 200b employing a microstrip line mode and a CPW mode, respectively, in accordance with one or more embodiments. FIGS. 2A and 2B both illustrate a signal conductor 202, ground conductor(s) 204, and a substrate (or medium) 206, as well as example E field lines (arrows 208) and H field lines (arrows 210) extending there between. As depicted in FIG. 2A, a relatively large amount of the E field lines penetrate the substrate 206 (e.g., as indicated by the arrows 208 extending from the signal conductor 202 to the ground conductor 204), with some of the H field lines passing through a portion of the substrate 206 (e.g., as indicated by only the lower portion of the H-field arrows 210 extending through the substrate 206 from the signal conductor 202 to the ground conductor 204). As depicted in FIG. 2B, a relatively small amount of the E field lines penetrate the substrate 206 (e.g., as indicated by only the lower portion of the arrows 208 extending through the substrate 206 from the signal conductor 202 to the ground conductors 204 on either side). As indicated in FIGS. 2A and 2B, in both microstrip line mode and CPW mode, a similar portion of the H field may penetrate the substrate 206 (e.g., as indicated by the lower half of the arrows 210 extending through the upper portion of the substrate 206 that is adjacent to the conductors 202).

Figure 3:
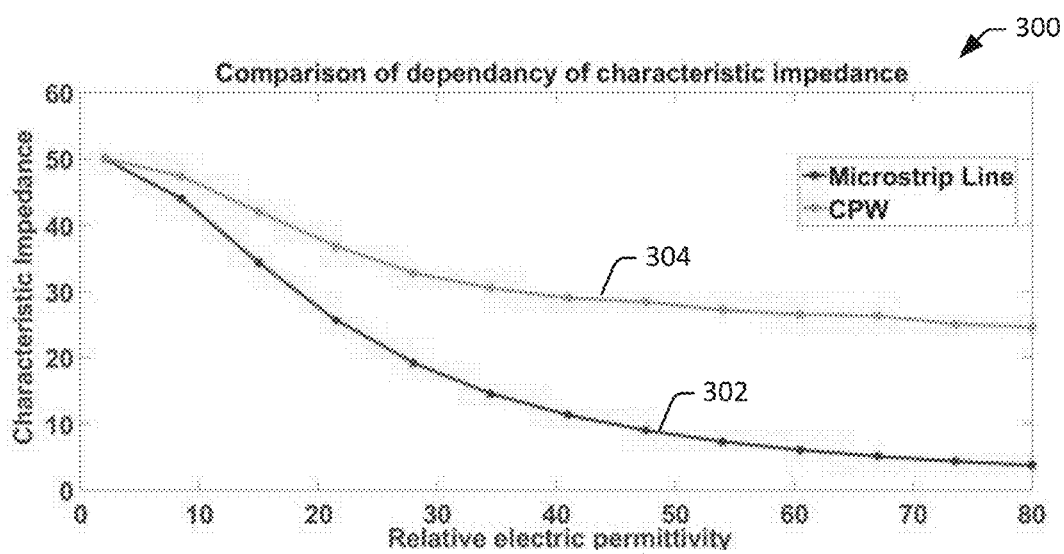
FIG. 3 is a plot diagram that illustrates values of characteristic impedance of a standard microstrip line and co-planer waveguide modes in accordance with one or more embodiments.

To verify the above described effect quantitatively, a model (e.g., an high frequency structural simulator (HFSS) model) can be generated for the microstrip line mode and/or the CPW mode. FIG. 3 is a plot diagram 300 that illustrates values of characteristic impedance (Ω or $Z_0$) of a standard microstrip line and CPW modes as a function of substrate permittivity at 200 MHz (megahertz) in accordance with one or more embodiments. The lower line in the diagram 302 represents the characteristic impedance (Ω or $Z_0$) as a function of relative electric permeability for a microstrip line mode, and the upper line in the diagram 304 represents the characteristic impedance (Ω or $Z_0$) as a function of relative electric permeability for a CPW mode. The illustrated embodiment may correspond to a substrate having a thickness of about 1.6 mm (millimeters). The diagram 300 illustrates the real part of characteristic impedance ($Z_0$) of both TL modes matched to 50 ohms at a relative electric permeability ($\in_r$) of about 2 for the medium, which is typical for oils. As can be seen, the CPW mode may be less affected by the shape/thickness of the substrate than the microstrip mode. This may be attributable to a relatively low amount of the field lines for the CPW penetrating the substrate. Thus, CPW may be suitable for wrapping the conductors around a non-planar structure, such as a three-dimensional (3D) cylindrical pipe surface. In some embodiments, the dependency of microstrip mode the geometric structure of substrate may be resolved using a dual ground plane microstrip TL, such as that described herein (e.g., a WC sensor for a pipe that includes a signal conductor (e.g., a T-resonator) disposed on one side of the substrate, and a ground conductor disposed on an opposite side of the substrate).

Figure 4:
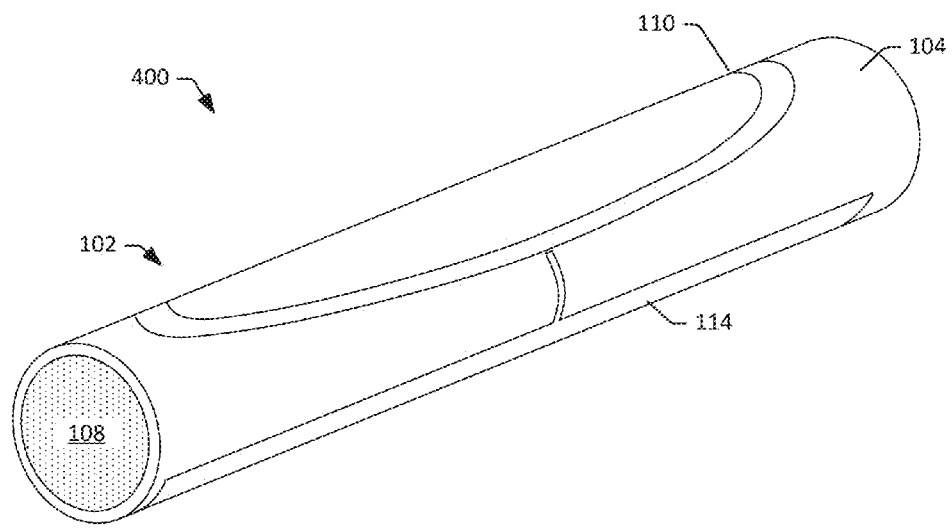
FIG. 4 is a diagram that illustrates an example ring resonator microstrip line based microwave resonator system in accordance with one or more embodiments.
Figure 5:
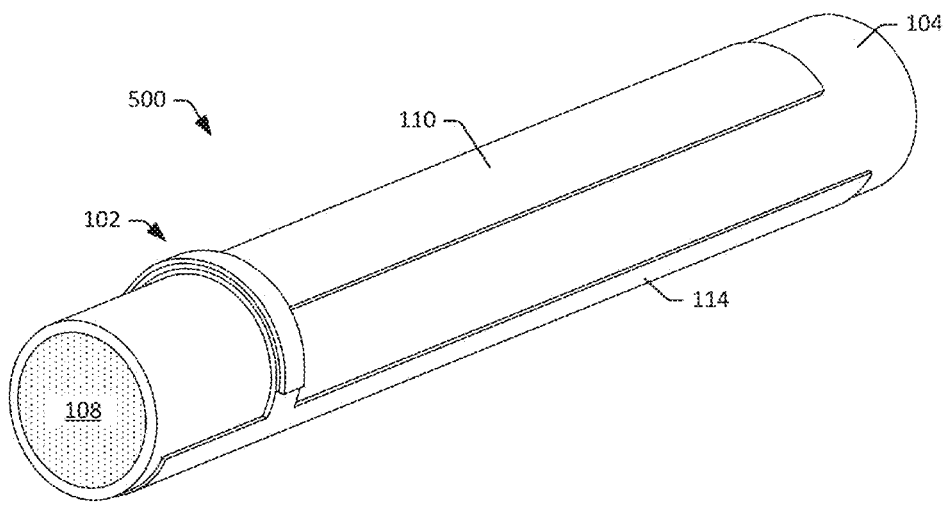
FIG. 5 is a diagram that illustrates an example T-resonator microstrip line based microwave resonator system in accordance with one or more embodiments.

In some embodiments, different types of microstrip line based microwave resonators can be implemented, such as a ring resonator (e.g., a circular resonator or an elliptical resonator) or an open/short circuited stub resonator (e.g., a T-resonator). FIG. 4 is a diagram that illustrates an example ring resonator microstrip line based microwave resonator system (or "ring system") 400 in accordance with one or more embodiments. FIG. 5 is a diagram that illustrates an example T-resonator microstrip line based microwave resonator system (or "T-resonator system") 500 in accordance with one or more embodiments. Referring to at least FIG. 4 the ring system 400 may include a WC sensor 102 having a ring shaped (e.g., circular or elliptical) signal conductor 110 disposed on one side (e.g., a first/upper/top side) of a pipe 104, and a ground conductor 114 (e.g., generally rectangular in shape) disposed on an opposite side (e.g., a second/lower/bottom side) of the pipe 104. Referring to at least FIG. 5 the T-resonator system 500 may include a WC sensor 102 having a T-shaped signal conductor 110 (e.g., having a feed line (FL) and an open shunt stub (SS)) disposed on one side (e.g., a first/upper/top side) of a pipe 104, and a ground conductor 102 (e.g., generally rectangular in shape) disposed on an opposite side (e.g., a second/lower/bottom side) of the pipe 104. Although certain embodiments are described herein with regard to a T-resonator type signal conductor 110 for the purpose of illustration, embodiments may include any suitable type/shaped signal conductor 110. For example, embodiments can be employed using a ring type signal conductor 110, or other suitable type/shape signal conductor 110, in place of or in conjunction with a T-resonator type signal conductor 110.

Figure 6:
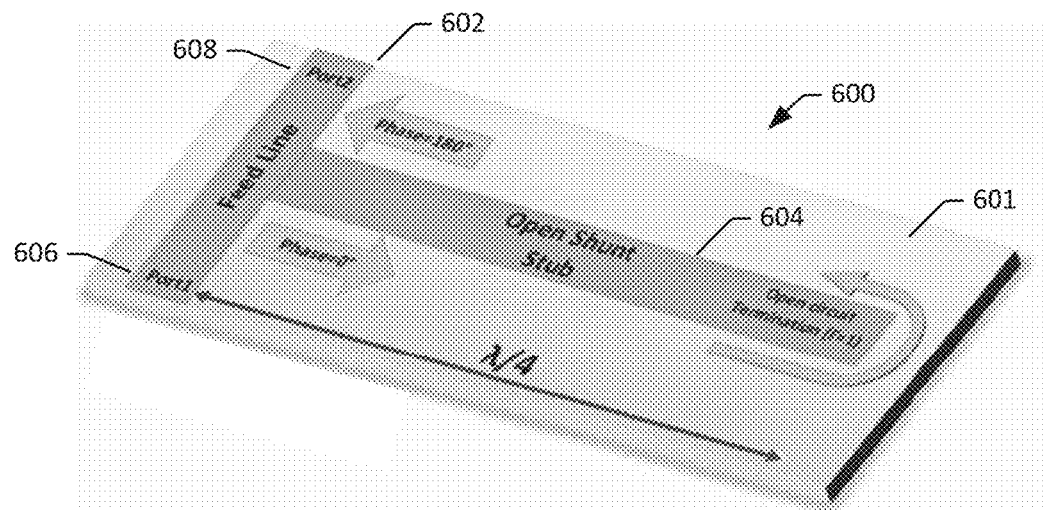
FIG. 6 is a diagram that illustrates example components of a T-resonator in accordance with one or more embodiments.

A T-resonator may include a transmission line (TL) (used for feeding and receiving microwave energy) shunted with either $\lambda/4$ length of open circuited or $\lambda/2$ length of short circuited stub. A $\lambda/4$ open circuited stub may be relatively short in size (for a given operational frequency) and, in some instances may be implemented without requiring any via. FIG. 6 is a diagram that illustrates example components of a T-resonator 600 laid flat on a substrate 601 in accordance with one or more embodiments. As depicted, the T-resonator 600 may include a conductive material of a "T" shape, having a feed line (FL) 602 and an open shunt stub (SS) 604. The feed line may include a first port 606 and a second port 608. The first port 606 may be used to introduce a signal (e.g., at a given frequency and phase) into the T-resonator 600. The second port may be used to sense a corresponding response signal (e.g., having a frequency and/or phase that may be different than the introduced signal). When deployed on a cylindrical pipe, the T-resonator 500 may take on a generally curved profile to that conforms to a surface of a pipe, as discussed in more detail herein with regard to at least FIGS. 10A-10E.

At resonance frequencies, an open shunt stub may appear as a short circuit after $\lambda/4$ transformation ($\pi$ radian rotation on the smith chart) in the middle of the transmission line. That is, incident and reflected waves may differ by about 180° (opposite in phase) at resonance frequencies, in the middle of transmission line, causing choke of signal transmission (e.g., due to destructive interference) between the ports. So, an S21 response (e.g., a response signal at the second port 508 due to a source signal introduced at the first port 506, representing the power transferred from the first port 506 to the second port 508) of the T-resonator may be characterized by dips at the resonance frequencies. A resonance frequency of a T-resonator can indicate the dielectric constant ($\in_r$) of the substrate, and a guided wavelength ($\lambda_g$) can indicate the resonance frequency of a T-resonator. Based on these relationships, the guided wavelength ($\lambda_g$) and/or the resonance frequency of a T-resonator may be utilized to find an unknown dielectric constant ($\in_r$) and loss of a medium (e.g., the dielectric constant ($\in_r$) and loss of an oil/water mixture flowing through a pipe 300 on which a microwave resonator, including a T-resonator similar to T-resonator 500, is disposed).

As discussed herein, embodiments of a WC sensor employing a microwave resonator system may include wrapping a signal conductor of a T-resonator on circumference of upper semi-cylindrical pipe surface and ground conductor on lower semi-cylindrical surface. In such an embodiment, several factors may be considered, including the following:

a) guided wavelength ($\lambda_g$) of the open shunt stub (SS) ($\lambda_{g\text{-}ss}$);

b) characteristic impedance ($Z_0$) of the open shunt stub (SS) ($Z_{0\text{-}SS}$); and c) characteristic impedance ($Z_0$) of the feed line (FL) ($Z_{0\text{-}FL}$).

With regard to the guided wavelength ($\lambda_g$) of an open shunt stub, the wavelength of microwaves in a medium can be defined as follows:

$$\lambda_g = \frac{\lambda_O}{\sqrt{\varepsilon_{\it eff}}} \qquad (3)$$

where $\lambda_O$ is a free space wavelength, and $\varepsilon_{\it eff}$ is the effective permittivity of the dielectric medium through which the microwave is traveling and depends upon the fringing field pattern defined by the placement of signal and ground conductors. The effective permeability ($\varepsilon_{\it eff}$) may depend upon the following parameters:

a) a distance between signal and ground conductor; and b) a dielectric constant ($\varepsilon_r$) of the substrate.

For the open shunt stub, the distance between ground and signal conductor may remain fixed so the guided wavelength ($\lambda_g$) may depend only on a dielectric constant ($\varepsilon_r$) of the substrate (e.g., the mixture inside the pipe). An increase in WC (e.g., an increase in the proportion of water to oil in the mixture) may cause the effective permeability ($\varepsilon_{\it eff}$) to increase and/or the guided wavelength ($\lambda_g$) to decrease. Consequently same physical length of shunt stub of T-resonator may appear electrically larger at a high WC, with a decreased resonance frequency.

Figure 7:
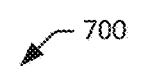
FIG. 7 is a table that illustrates example simulation results of parametric study of the effect of the characteristic impedance of the open shunt stub ($Z_{O-SS}$) of a T-resonator on performance of the T-resonator in accordance with one or more embodiments.

With regard to the characteristic impedance ($Z_0$) of the open shunt stub (SS) ($Z_{0-SS}$), similar to $\lambda g$, the characteristic impedance of the open shunt stub ($Z_{0-SS}$) can also depend upon the effective permeability ($\varepsilon_{\it eff}$). The characteristic impedance of the open shunt stub ($Z_{0-SS}$), however, may not have any pronounced effect on the performance of the T-resonator. This can be verified by a parametric study investigating the effect of the characteristic impedance of the open shunt stub ($Z_{0-SS}$) on performance of a simple flat substrate based T-resonator. FIG. 7 is a table 700 that illustrates example simulation results of parametric study of the effect of the characteristic impedance of the open shunt stub ($Z_{0-SS}$) of a T-resonator on performance of the T-resonator in accordance with one or more embodiments. The table 700 may illustrate that good signal rejection (dip) in S21 response (at $f_0$) can be achieved (e.g., $f_0$ can be identified) irrespective of the characteristic impedance of the open shunt stub ($Z_{0-SS}$). Moreover, the effective permeability ($\varepsilon_{\it eff}$) increases, approaching dielectric constant ($\varepsilon_r$), for decreasing values of the characteristic impedance of the open shunt stub ($Z_{0-SS}$). This may be attributable to field lines becoming denser in the substrate, resulting in f0 shifting towards lower frequencies.

In some embodiments of a T-resonator implemented on a pipe surface, the physical width of shunt stub may be constant along its length. As demonstrated by the values in the table 700 of FIG. 7, in such an embodiment, with an increase in WC (e.g., an increase in the proportion of water to oil in the mixture) which appears as an increase in the effective permeability ($\varepsilon_{\it eff}$), the characteristic impedance of the open shunt stub ($Z_{0-SS}$) may decrease, the width of the shunt stub may appear to increase, and the resonance frequency ($f_0$) may decrease. That is, increasing WC (e.g., increasing the effective permeability ($\varepsilon_{\it eff}$)) can cause a decrease in the guided wavelength ($\lambda_g$) and the characteristic impedance of the open shunt stub ($Z_{0-SS}$), and, as a result, a decrease in the resonance frequency ($f_0$) of the resonator.

With regard to the characteristic impedance ($Z_0$) of the feed line (FL) ($Z_{0-FL}$), since feed line can be utilized to provide and/or receive the microwave signal from the open shunt stub, it may be matched to about 50Ω (the characteristic impedance ($Z_0$) of most of measurement equipment) to avoid mismatch losses which can negatively affect the WC sensor's performance.

In some embodiments, the characteristic impedance of the feed line ($Z_{0-FL}$) may vary based on at least the following:

a) the variable distance between the signal conductor and the ground conductor, and b) the variable dielectric constant ($\varepsilon_r$) of the mixture inside the pipe.

As discussed herein, in some embodiments, a separate ring shaped ground (or "ground ring") for the feed line can be included. Such a ground ring may eliminate, or otherwise reduce, the effect that the variable distance between the signal conductor and the ground conductor and/or the variable dielectric constant ($\varepsilon_r$) of the mixture inside the pipe has on the characteristic impedance of the feed line ($Z_{0-FL}$). In some embodiments, this supplemental ground plane (or ground ring), may be disposed between the curved feed line and the surface of a cylindrical pipe, and may connect with a main ground plane (or "bottom" ground plane) (GP) of the ground conductor. In some embodiments, the feed line and the ground ring may be separated by a dielectric separator. Example embodiments of ground rings and dielectric separators are discussed in more detail herein with regard to at least FIGS. 10A-10E.

As discussed herein, a T-resonator based WC sensor can be employed on a variety of different sized pipes. This can be advantageous in the oil and gas industry, for example, as WC measurements may be taken for fluid flowing through a variety of different sized pipes (e.g., pipes up about 1500 mm in diameter, or more). In an example embodiment, a pipe may have an internal diameter of about 46 mm and an outer diameter of about 50 mm. Although the length of the pipe may vary by application, a T-resonator based WC sensor may be disposed, for example, on a given length of the pipe (e.g., across about 350 mm of the pipe's length).

For shorter lengths, a majority of the fields from the open shunt stub may terminate at the ground ring which may severely affect the resonance sensing phenomenon. The length of the open shut stub may also determine the operational range of the WC sensor. In some embodiments, the open shunt stub may have a length that is the same or greater than the diameter of the pipe (which is about the separation between the open shunt stub and the main ground plane of the ground conductor). For example, in the above described embodiment, the open shunt stub may have a length that is greater than about 50 mm. In some embodiments, the length may be up to several times the diameter of the pipe. For example, the open shunt stub may have a length that is about three to five times longer than the diameter of the pipe (e.g., about 3× to 5× the separation between open shunt stub and the main ground plane of the ground conductor). For example, in the above described embodiment, the open shunt stub may have a length that is about 250 mm (or about 5× the OD of the pipe). A length of about 250 mm may, for example, provide an operating range of about 80 MHz-190 MHz.

As discussed here, the width (or arc length) of the open shunt stub may determine its characteristic impedance ($Z_{0-SS}$), but the actual characteristic impedance ($Z_{0-SS}$) may vary as the dielectric constant ($\varepsilon_r$) of the substrate varies (e.g., in the presence of different oil and water mixtures). Continuing with the above example, including an open shunt stub having a length of about 250 mm, the shut stub may have a width of about 25.4 mm to provide a characteristic impedance of the open shunt stub ($Z_{0-SS}$) of about 50Ω. If an average distance between the signal conductor and ground plane is considered to be about to be 45 mm, along with an effective permeability ($\in_{eff}$) variation of about 2-80, then this width of about 25.4 mm may correspond to characteristic impedance of the open shunt stub ($Z_{O\text{-}SS}$) between about 108Ω-20Ω (e.g., similar to the same range provided in table 700 of FIG. 7).

In some embodiments, the length of the feed line can be about the same or greater than the width of the shunt stub. Continuing with the above example, including a shunt stub having a width of about 25.4 mm, the length of the feed line may be about 45 mm. In some embodiments, the width of the feed line can be dimensioned to achieve a desired characteristic impedance. Continuing with the above example, the width of the feed line may be about 2.5 mm to provide a characteristic impedance of the feed line ($Z_{O\text{-}FL}$) of about 50Ω.

In some embodiments, the width of the ground ring can be dimensioned to be the same or greater than the width of the feed line. For example, the width of the feed line may be about 2.5 times the width of the feed line. Continuing with the above example, including a feed line width of about 2.5 mm, the width of the ground ring may be about 6.3 mm.

In some embodiments, the separator can be dimensioned to provide physical and/or electrical isolation between the feed line and the ground ring. The width of the ground ring can be dimensioned to be about the same or greater than the width of the feed line and/or the ground ring. Continuing with the above example, including a ground ring having a width of about 6.3 mm, the width of the separator may be about 6.3 mm. In some embodiments, the length of the separator may be about the same or greater than the length of the feed line. Continuing with the above example, including a feed line length of about 45 mm, the length of the separator may be about 45 mm. In some embodiments, the separator may be of a sufficient thickness to provide physical and/or electrical isolation between the feed line and the ground ring. Continuing with the above example, the separator may have a dielectric constant ($\in_r$) of about 2.8 and a constant thickness of about 1 mm. Such a constant thickness separator may provide a constant separation distance between the feed line and the ground ring.

In some embodiments, the ground plane (GP) can be dimensioned to provide a field pattern that encompasses a relatively large amount of a cross-sectional area inside the pipe. Such a pattern may enable the field to pass through a relatively large portion of the medium flowing through the pipe (e.g., across the entirety of the cross-sectional area of the pipe) to provide an accurate representation of the medium flowing through the pipe as a whole, as opposed to the field passing through only portions of the flow (e.g., in the upper portion of cross-sectional area of the pipe) which may only provide a representation of the medium flowing through those limited portions of the pipe.

Figure 8A:
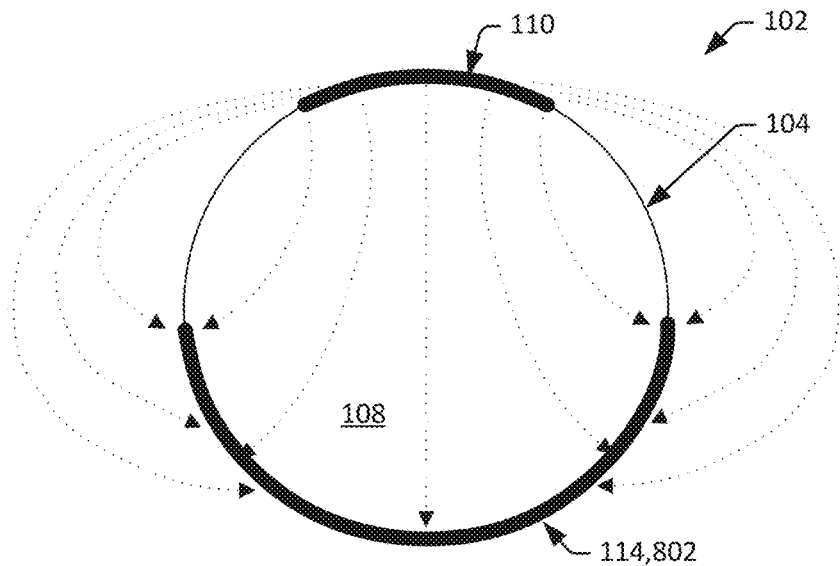
FIG. 8A is a diagram that illustrates field lines extending from a signal conductor to a relatively wide ground plane of a ground conductor on a pipe in accordance with one or more embodiments.

Referring to FIG. 8A, which is a diagram that illustrates field lines extending from a signal conductor 110 to a relatively wide "bottom" or "main" ground plane 802 of a ground conductor 114 on a pipe 104 in accordance with one or more embodiments, a ground plane 802 with a relatively large width (e.g., having an arc length spanning a greater portion of the curvature of the second/lower/bottom side of the pipe 104), may cause a larger number of the field lines to terminate at or near the edges of the ground plane 802, with a smaller number of the field lines terminating on the central/bottom portion of the bottom ground plane 802. As a result, the field lines may pass through the upper/outside edges of the interior of the pipe 104, but may not cross through the lower/center portion of the interior pipe 104. Such an embodiment (e.g., incorporating a relatively wide ground plane 802) may be sensitive to relative percentage change of oil and water which occurs in the edge/side portions of the interior of the pipe 104, but may not be very sensitive to relative percentage change of oil and water which occurs in the lower/central portion of the interior of the pipe 104.

Figure 8B:
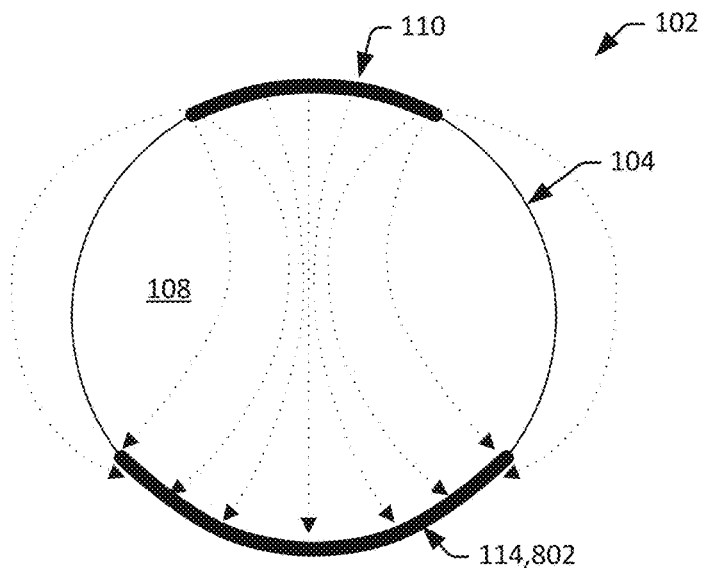
FIG. 8B is a diagram that illustrates field lines extending from a signal conductor to a relatively narrow ground plane of a ground conductor on a pipe in accordance with one or more embodiments.

Referring to FIG. 8B, which is a diagram that illustrates field lines extending from a signal conductor 110 to a relatively narrow ground plane 802 of a ground conductor 114 on a pipe 104 in accordance with one or more embodiments, a ground plane 802 with a relatively small width (e.g., having an arc length spanning a lesser portion of the curvature of the second/lower/bottom side of the pipe 104), may cause the field lines to pass primarily through the central portion of the interior pipe 104 and terminate along the ground plane 802, with a smaller number of the field lines extending through the edge/side portions of the interior of the pipe 104. As a result, the field lines may pass through the lower/center portion of the interior of the pipe 104, but may not pass through the edge/side portions of the interior of the pipe 104. Such an embodiment (e.g., incorporating a relatively narrow ground plane 802) may be sensitive to relative percentage change of oil and water which occurs in the lower/central portion of the interior of the pipe 104, but may not be very sensitive to relative percentage change of oil and water which occurs in the edge/side portions of the interior of the pipe 104. Accordingly, the width (or "arc length") of the ground plane 802 can play significant role in the performance of a WC sensor. As described herein, embodiments may employ a ground plane having a width that reduces fringing of the field and, thus, provides improved sensitivity. That is, a ground plane may be of an optimum size (e.g., to provide field lines that are similar to that shown in FIG. 8B) to provide improved performance.

In some instances, a minimum fringing field point can depend on the medium inside the pipe 104. Given this dependency, a parametric study on the arc length size of the ground plane 802 can be conducted for at least two extreme cases (e.g., a pipe filled with water and pipe filled with oil), and the study may be used to determine the arc length (e.g., the width) of the ground plane 802 to be used. Starting from an arc length of about 64 mm, for example, the arc length of the ground plane 802 may be decreased and tested iteratively, in an effort to expose a valley point where a minimum resonance frequency of T resonator occurs. Decreasing the size of ground plane 802 may cause decrement in fringing through air and increment in the effective permeability ($\in_{eff}$) experienced for a T-resonator. This may, in turn, decrease the resonance frequency as explained above. Moreover, decreasing the arc length of the ground plane 802 beyond the valley point may causes the E fields to terminate at the ground ring instead of the ground plane 802 (e.g., as described with regard to FIG. 8A). Decreasing the arc length of the ground plane 802 beyond the valley point may also hinder the propagation of microwaves along the full length of the shunt stub, causing an increase in resonance frequency. A smaller ground plane 802 created by decreasing the ground plane arc length beyond the valley point can also cause radiation loss, which may be undesirable. This being said, it may be desirable to employ a ground plane 802 having an arc length that corresponds the valley for a particular medium inside the pipe.

Figure 9A:
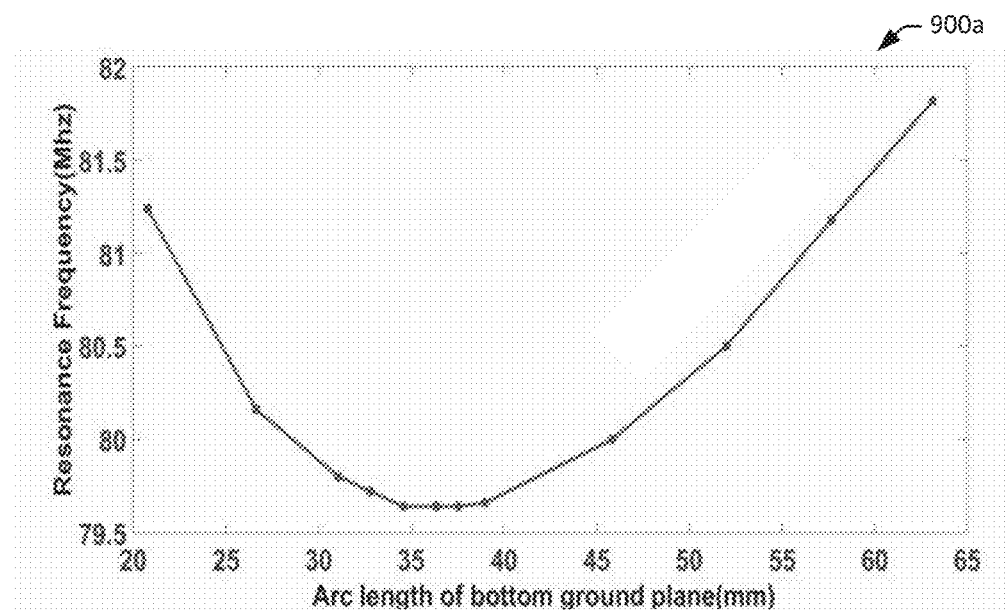
FIG. 9A is a plot diagram that illustrates example results for resonance frequency versus different arc lengths (or widths) of a ground plane employed on a pipe filled with water in accordance with one or more embodiments.

FIG. 9A is a plot 900a that illustrates example results for resonance frequency versus different arc lengths of a ground plane employed on a pipe filled with water in accordance with one or more embodiments. A valley point (or range) for a water filled pipe may occur where a slope of the curve is about zero. In the illustrated embodiment, the valley point (or range) may be determined to occur at an arc length of about 35-40 mm.

Figure 9B:
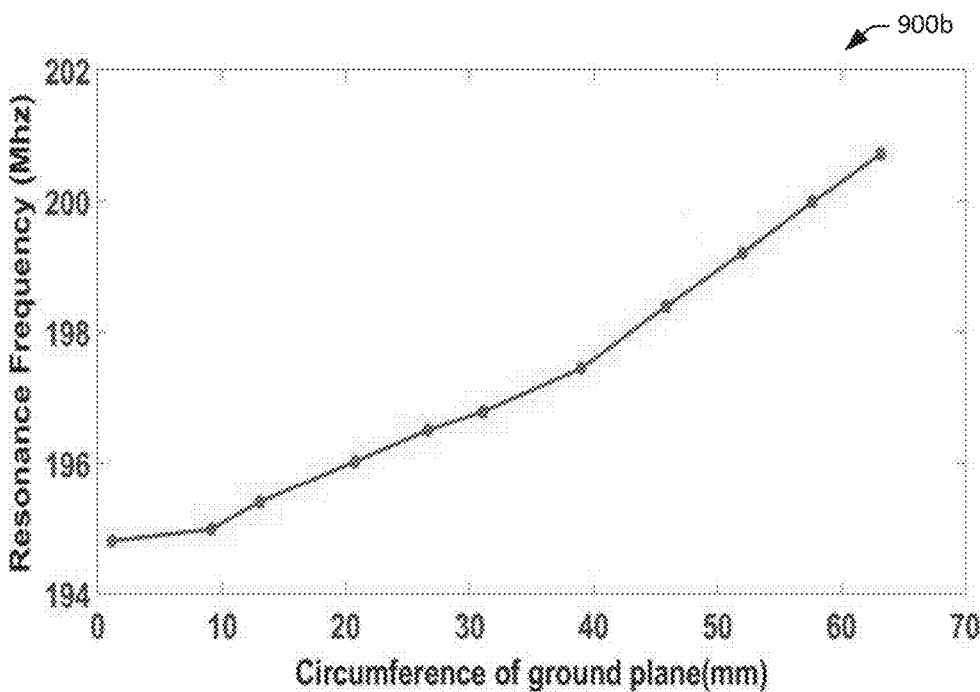
FIG. 9B is a plot diagram that illustrates example results for resonance frequency versus different arc lengths (or widths) of a ground plane employed on a pipe filled with oil in accordance with one or more embodiments.

FIG. 9B is a plot 900b that illustrates example results for resonance frequency versus different arc lengths of a ground plane employed on a pipe filled with oil in accordance with one or more embodiments. Fringing fields may be less common for the case of water because of its higher electric permittivity, but may be less common for the case of oil because due to its lower electric permittivity. Although the plot 900b does not appear to illustrate a well-defined valley point (or range) in case of oil, in the illustrated embodiment, the valley point (or range) may be determined to occur at an arc length of about 2-10 mm. In some embodiments, the arc length of a ground plane employed on a WC sensor for sensing WC of a mixture of fluids may be determined based on arc lengths determined for some or all of the fluids present in the mixture. For example, the arc length of the ground plane may be determined as the average of the arc length determined for each of the fluids in the mixture. Continuing with the above example, where a first arc length of about 37.5 mm is determined for the case of a pipe filled with water (e.g., an average of the arc length range of about 35-40 mm) and a second arc length of about 6 mm is determined for the case of a pipe filled with oil (e.g., an average of the arc length range of about 2-10 mm), the arc length for the ground plane for a WC sensor used to measure WC of a mixture of water and oil may be determined to be about 22 mm (e.g., ([(35+40)/12]+[(2+10)/2])/2). In such an embodiment, the ground plane of a WC sensor for use in detecting water-cut of a mixture of oil and water in a pipe having an outside diameter of about 50 mm may have an arc-length (or width) of about 22 mm (e.g., about 14% of the pipe circumference).

In some embodiments, the ground plane may have a length that is greater than the length of the resonator. Continuing with the above example with a pipe having an outer diameter of 50 mm and the open shunt stub having a length of about 250 mm in, the ground plane (GP) may have a length of about 300 mm. The length of "bottom" ground plane should be sufficient enough only to span the area of overlying T-resonator. A longer bottom ground plane can affect the fringing field pattern, and hence the performance of the WC sensor. The length of the bottom ground plane may be scaled, e.g., to account for different pipe sizes.

Figure 10A:
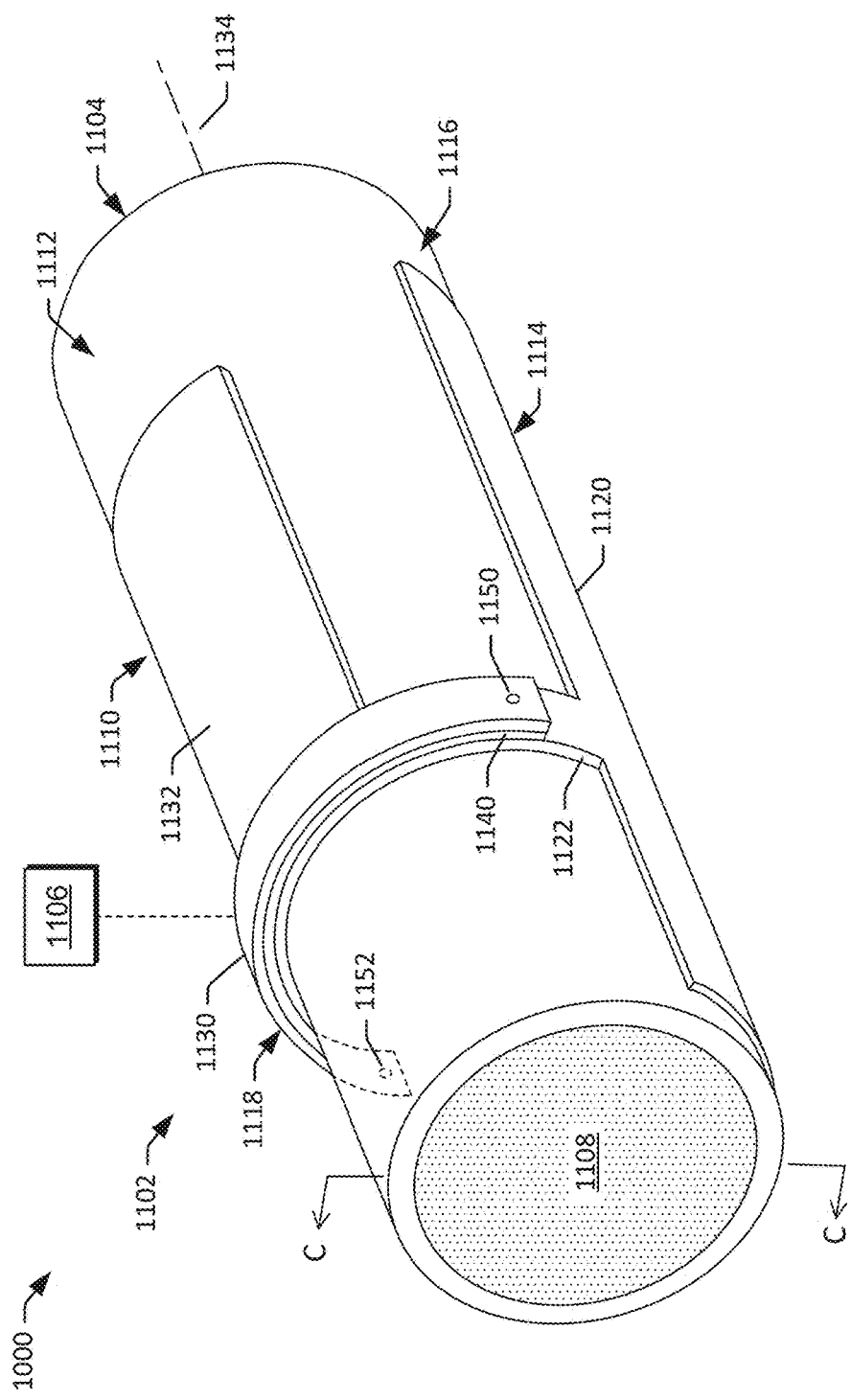
FIGS. 10A-E are diagrams that illustrate of various views of an example embodiment of a water-cut sensing system in accordance with one or more embodiments.
Figure 10B:
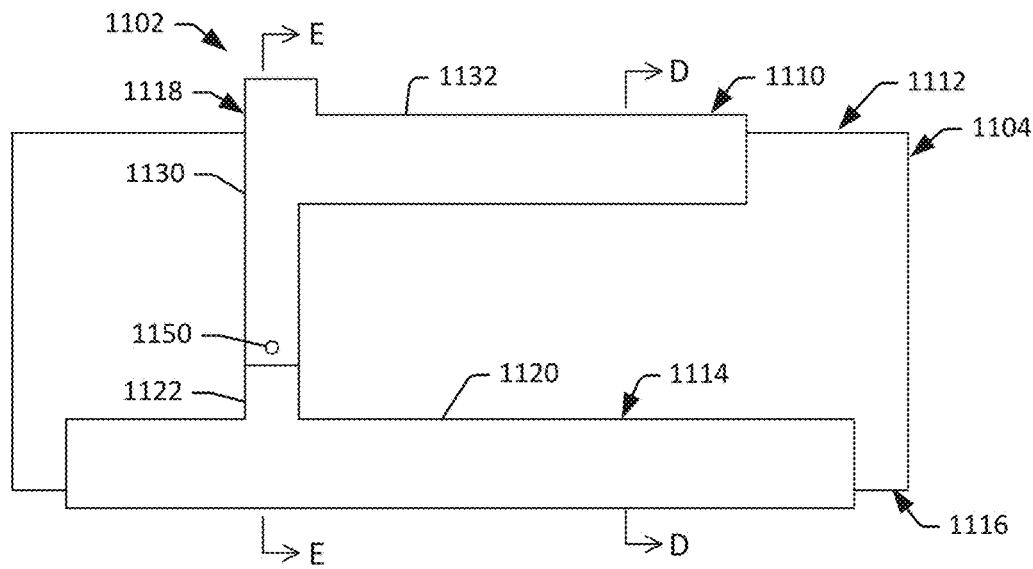
Figure 10C:
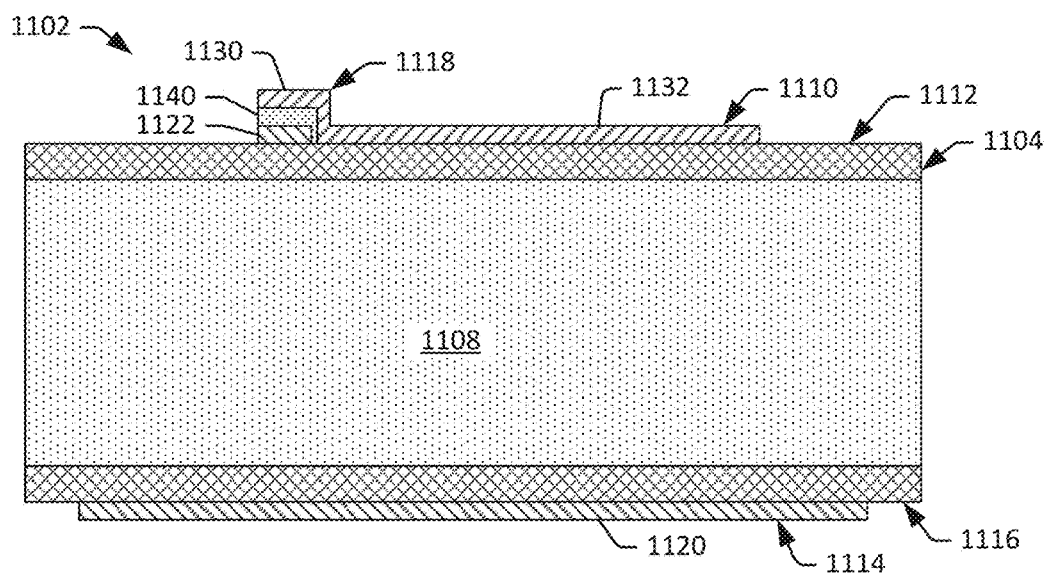
Figure 10D:
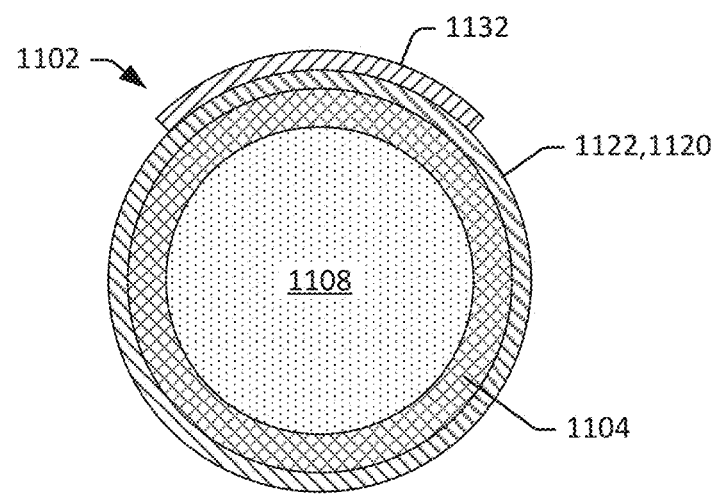
Figure 10E:
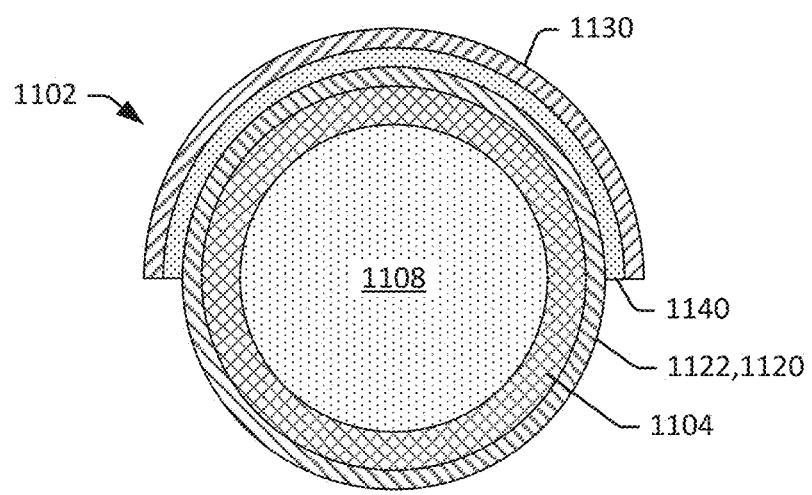

FIGS. 10A-E are diagrams that illustrate of various views of an example embodiment of a water-cut (WC) sensing system 1000 in accordance with one or more embodiments. More specifically, FIG. 10A is an isometric view of the WC sensing system 1000, FIG. 10B is an side view of the WC sensing system 1000, FIG. 10C is a cross-sectional side view of the WC sensing system 1000 taken along the line C-C of FIG. 10A, FIG. 10D is a cross-sectional end view of the WC sensing system 1000 taken along the line D-D of FIG. 10B, and FIG. 10E is a cross-sectional end view of the WC sensing system 100 taken along the line E-E of FIG. 10B.

In some embodiments, the WC sensing system 1000 includes a water-cut (WC) sensor 1102, a cylindrical pipe 1104, and/or a measurement processing system 1106. As discussed herein, the water-cut (WC) sensor 1102 may be disposed on (or otherwise integrated with) the cylindrical pipe 1104. In some embodiments, the WC sensor 1102 can include a first/signal conductor (SC) 1110 (e.g., a first conductive plane), such as a T-resonator, disposed at a first/upper/top surface 1112 of the cylindrical pipe 1104, and a ground conductor (GC) 1114 (e.g., a second conductive plane) disposed at a second/lower/bottom surface 1116 of the cylindrical pipe 1104 that is opposite the first/upper/top surface 1112 of the pipe 1104. In such a configuration, the WC sensing system 1100 may be employed to sense a water-cut of a fluid 1108 (e.g., a water and oil mixture, or other substrate) flowing through or otherwise present in the section of the pipe 1104 at or near the location where the WC sensor 102 is disposed on the pipe 1104.

In some embodiments, the signal conductor 1110 may include a T-resonator 1118. For example, the signal conductor 1110 may include a T-resonator 1118 including a sheet of generally "T" shaped conductive material (e.g., copper) disposed along the length of the first/upper/top surface 1112 of the pipe 1104. The ground conductor 1114 may include a "main" or "bottom" ground plane (GP) 1120 and a ground ring (GR) 1122. The ground plane 1120 may be a generally rectangular shaped conductive sheet of material (e.g., copper) that is disposed along the length of the second/lower/bottom surface 1116 of the pipe 1104. The ground plane 1120 may be arranged to extend longitudinally, along the length of the surface of the pipe 1104 (e.g., parallel to the longitudinal axis 1134 of the pipe 1104). The ground ring 1122 may include a band of conductive sheet of material (e.g., copper) that is disposed (e.g., wrapped) around the circumference (e.g., the outer diameter) of the pipe 1104. The ground ring 1122 may be arranged to extend laterally, about the circumference of the pipe 1104 (e.g., perpendicular to a longitudinal axis 1134 of the pipe 1104).

In some embodiments, a portion of the T-resonator 1118 of the signal conductor 1110 may at least partially overlap a portion of the ground ring 1122 of the ground conductor 1114. For example, the T-resonator 1118 may include a feed line (FL) 1130 and an open shunt stub (SS) 1132. The feed line 1130 may include the "top" portion of the "T" shape of the T-resonator 1118, and the open shunt stub 1132 may include the "bottom" portion of the "T" shape of the T-resonator 1118. The feed line 1130 may be arranged to extend laterally, about the circumference of the pipe 1104 (e.g., perpendicular to a longitudinal axis 1134 of the pipe 1104). The open shunt stub 1132 may be arranged to extend longitudinally, along the length of the surface of the pipe 1104 (e.g., parallel to the longitudinal axis 1134 of the pipe 1104). The feed line 1130 may wrap about an upper portion of the circumference of the pipe 1104 by a first amount, and the open shunt stub 1132 may wrap about an upper portion of the circumference of the pipe 104 by a second amount that is less than the first amount. The ground ring 1120 may similarly be wrapped about the circumference of the pipe 1104, including around at least the upper portion of the pipe 1104 about which the feed line 1130 is wrapped. Further, in some embodiments, the feed line 1130 of the T-resonator 1118 may overlap at least a portion of the ground ring 1118, such that at least this portion of the ground ring 1118 is disposed between feed line 1130 and the surface of the pipe 1104. That is, at least this portion of the ground ring 1120 may be "sandwiched" between the feed line 1130 and the surface of the pipe 1104.

In some embodiments, a dielectric separator 1140 may be provided between at least the overlapping portions of the signal conductor 1110 and the ground conductor 1114 to physically and/or electrically isolate them from one another. For example, a dielectric separator 1140 may include a strip of dielectric material (e.g., a Teflon strip) about the size of (or larger than) the feed line 1130 that is disposed between the feed line 1130 and the overlapped portion of the ground ring 1122 to maintain physical and/or electrical isolation of the signal conductor 1110 (e.g., including the T-resonator 1118) and the ground conductor 1114. In some embodiments, the dielectric separator 1140 may be of a constant thickness (e.g., about 1 mm) to maintain a constant distance between the overlapping portions of the signal conductor 1110 (e.g., including the T-resonator 1118) and the ground conductor 1114.

In some embodiments, the signal conductor 1110 may include a first/input port 1150 for input of a source signal of a first frequency and phase, and a second/output port 1152 for output of a corresponding response signal of a second frequency and phase. Continuing with the above example employing the T-resonator 1118, the first/input port 1150 may be located at or near a first end of the feed line 1130, and the second/output port 1152 may be located at or near a second end of the top portion of the feed line 1130 (opposite the first end). Electrical leads of the measurement processing system 1106 may be coupled to the ports 1150 and 1152 for introducing source signals and sensing response signals. For example, an input lead for introducing a source signal may extend from an output circuit of the measurement processing system 1106 to the first/input port 1150, and an output lead for sensing the response signal may extend from an input circuit of the measurement processing system 1106 to the second/output port 1152. As described herein, in some embodiments, the measurement processing system 1106 may provide and sense these respective signals and use the characteristics of the signals to determine a WC of the fluid 1108 in the pipe 1104.

In some embodiments, during use, the fluid 1108 (e.g., a production fluid including a mixture of oil and water) may flow through the center of the pipe 1104 such that the fluid 1108 passes between at least a portion of the signal conductor 1110 disposed on the first/upper/top surface 1112 of the pipe 1104 and at least a portion of the ground conductor 1114 disposed on the second/lower/bottom surface 1116 of the pipe 1104. For example, if the WC sensor 1102 is disposed on a length (or section) of the pipe 1104 used to transport production fluid including a mixture of oil and water) from a well, the production fluid may flow through the pipe 1104, between the signal conductor 1110 and the ground conductor 1114 which are generally disposed on opposite sides of the pipe 1104. In some embodiments, while the fluid 1108 is flowing through the pipe 1104 (or otherwise present in the pipe 1104), a source signal can be introduced into the signal conductor 1110, and a corresponding response signal present at signal conductor 1110 can be sensed. For example, a source signal of a first/predetermined frequency and phase can be introduced at the first/input port 1150, and a corresponding response signal of a second/resulting frequency and phase can be sensed at the second/output port 1152. As described herein, in some embodiments, the source signal may be generated by the measurement processing system 1106. For example, the measurement processing system 1106 may include a vector network analyzer (VNA), and the source signal may be generated by a source circuit, such as a signal generator, of the vector network analyzer (VNA). As describe herein, in some embodiments, the response signal may be sensed/measured by the measurement processing system 1106. For example, a sensing circuit, such as a receiver of the vector network analyzer (VNA), may receive the response signal. In some embodiments, the signals may be processed by the measurement processing system 1106 to determine various characteristics of the fluid 1108, such as the water-cut of the fluid 1108. For example, the measurement processing system 1106 may include a processor, such as a computer processor of the vector network analyzer (VNA) and/or other computing devices, that analyzes the characteristics of the source signal and/or the corresponding response signal to determine the resonance frequency of the WC sensor 1102 in the presence of the fluid 1108 (e.g., a resonance frequency of the T-resonator with the fluid 1108 currently flowing through or otherwise located in the pipe 1104, between the signal conductor 1110 and the ground conductor 1114). Based on a predetermined correlation between the water-cut of a fluid mixture flowing through the pipe 104 and the resonance frequency of the WC sensor 1102, the water-cut of the fluid 1108 flowing through the pipe 104 can be determined. That is, the water-cut of the fluid 1108 passing through the pipe 1108 can be determined based on the resonance frequency of the WC sensor 102 at or near the time when the fluid 1108 passes through the WC sensor 1102.

Figure 11A:
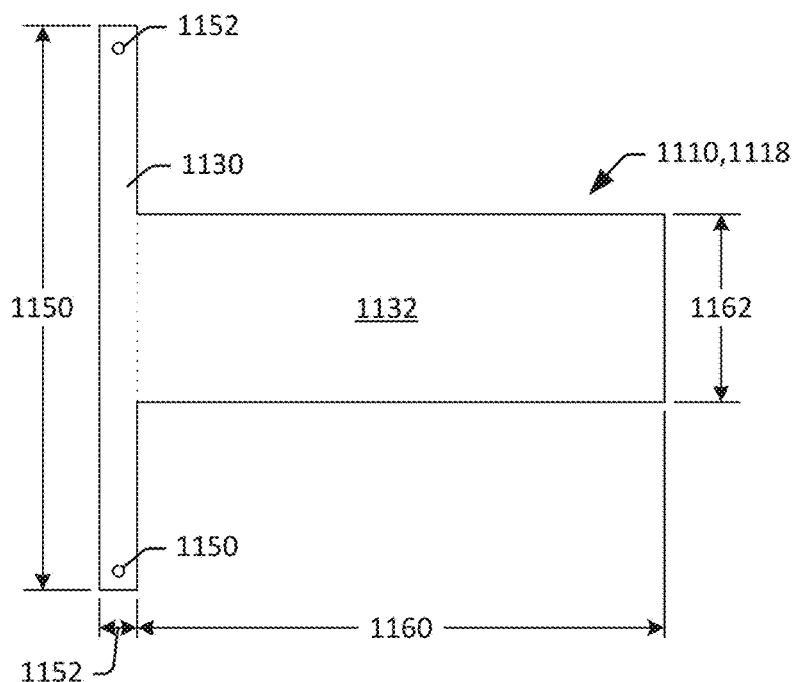
FIG. 11A is a diagram that illustrates a planar view of the T-resonator of FIGS. 10A-10E in accordance with one or more embodiments.
Figure 11B:
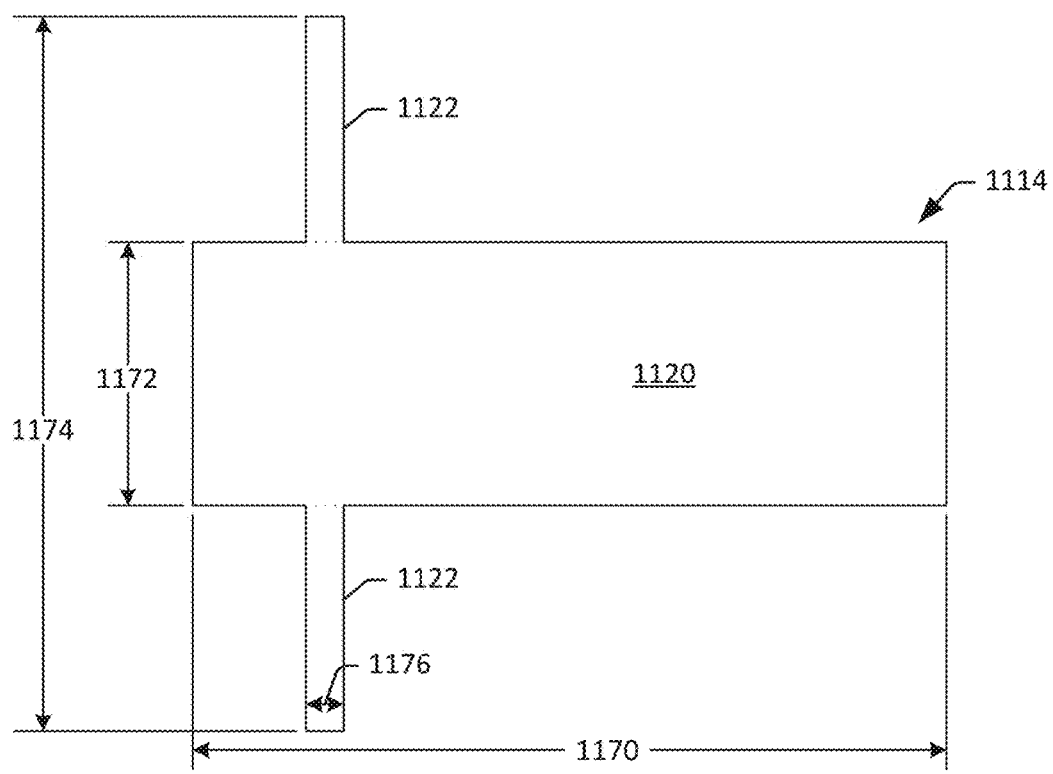
FIG. 11B is a diagram that illustrates a planar view of the ground conductor of FIGS. 10A-10E in accordance with one or more embodiments.

FIG. 11A is a diagram that illustrates a planar view of the T-resonator 1118 in accordance with one or more embodiments. This view may represent the planar shape of the T-resonator if it were laid flat (or "unwrapped"), as opposed to being disposed on the curved surface of the pipe 1104. FIG. 11B is a diagram that illustrates a planar view of the ground conductor 1114 in accordance with one or more embodiments. This view may represent the planar shape of the ground conductor 1114 if it were laid flat (or "unwrapped"), as opposed to being disposed on the curved surface of the pipe 1104, and the ground ring were "broken" as opposed to being contiguously wrapped about the pipe 1104.

In an example embodiment, the pipe 1104 may have an internal diameter of about 46 mm and an outer diameter of about 50 mm. Consistent with the dimensioning discussed above, and referring to FIG. 11A, the feed line 1130 may have a length (or arc length) 1150 of about 45 mm and a width 1152 of about 2.5 mm, and the open shunt stub 1132 may have a length 1160 of about 250 mm and a width (or arc length) 1162 of about 25.4 mm. With reference to FIG. 11B, the ground plane 1120 may have a length 1170 of about 300 mm and a width (or arc length) 1172 of about 22 mm, and the ground ring 1122 may have a length (or arc length) 1174 of about 157 mm (e.g., the circumference of the pipe 1104) and a width 1176 of about 6.3 mm. The separator 1140 may have a length (or arc length) of about 45 mm and a width of about 6.3 mm.

Figure 12:
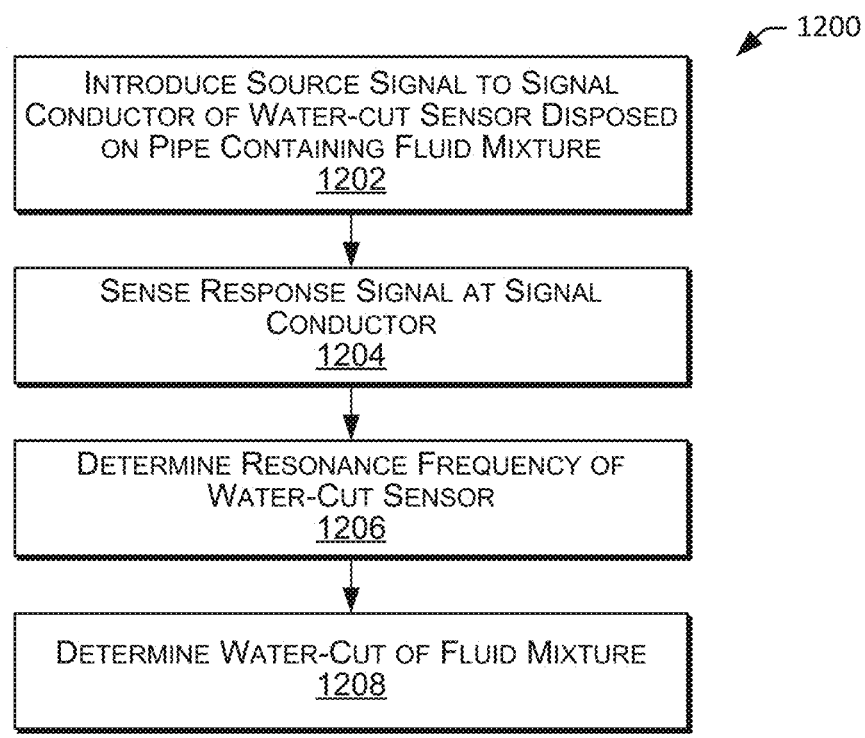
FIG. 12 is a flowchart that illustrates an example method of determining water-cut of a water-oil fluid mixture in a pipe using a microwave based water-cut sensor in accordance with one or more embodiments.

FIG. 12 is a flowchart that illustrates a method 1200 of determining water-cut of a water-oil fluid mixture in a pipe using a microwave based water-cut sensor in accordance with one or more embodiments. Method 1200 may generally include introducing a source signal at a signal conductor of a water-cut sensor disposed on a pipe having a fluid mixture therein (block 1202), sensing a response signal at the signal conductor (block 1204), determining a resonance frequency of the WC sensor based at least in part on the response signal (block 1206), and determining a water-cut for the fluid mixture based at least in part on the determined resonance frequency (block 1208). In some embodiments, some or all of the operations of the method 1200 may can be performed by the measurement processing system 106 (or 1106).

In some embodiments, introducing a source signal at a signal conductor of a water-cut sensor disposed on a pipe having a fluid mixture therein (block 1202) can include the measurement processing system 1106 driving a signal conductor 1106 of a water-cut sensor 1102 disposed on a pipe 1104 having a fluid 1108 therein with one or more source signals of different phase and/or frequencies. The source signals may be for example in the operational range of the WC sensor 1102 (e.g., about 50 MHz-130 Mhz).

In some embodiments, sensing a response signal at the signal conductor (block 1204), can include the measurement processing system 1106 sensing the phase and/or frequency of one or more response signals at another portion of the signal conductor 1110 that are generated as a result of the introduction of the one or more source signals.

Figure 15:
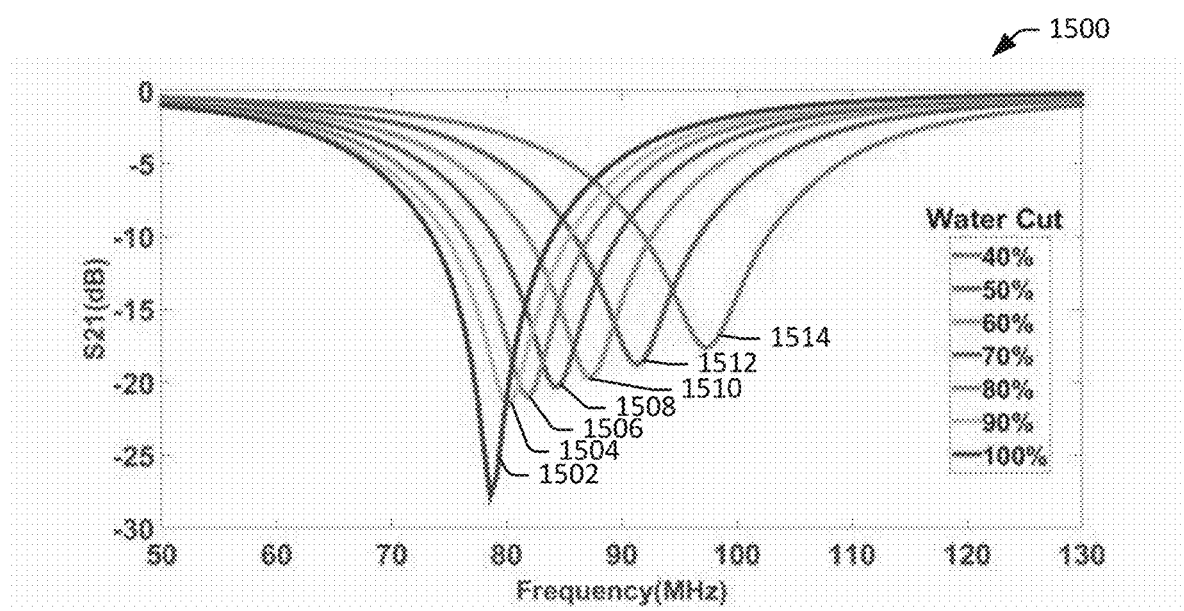
FIG. 15 is a plot diagram that illustrates example S21 responses of a water-cut sensor determined for fluids in a pipe in accordance with one or more embodiments.
Figure 16A:
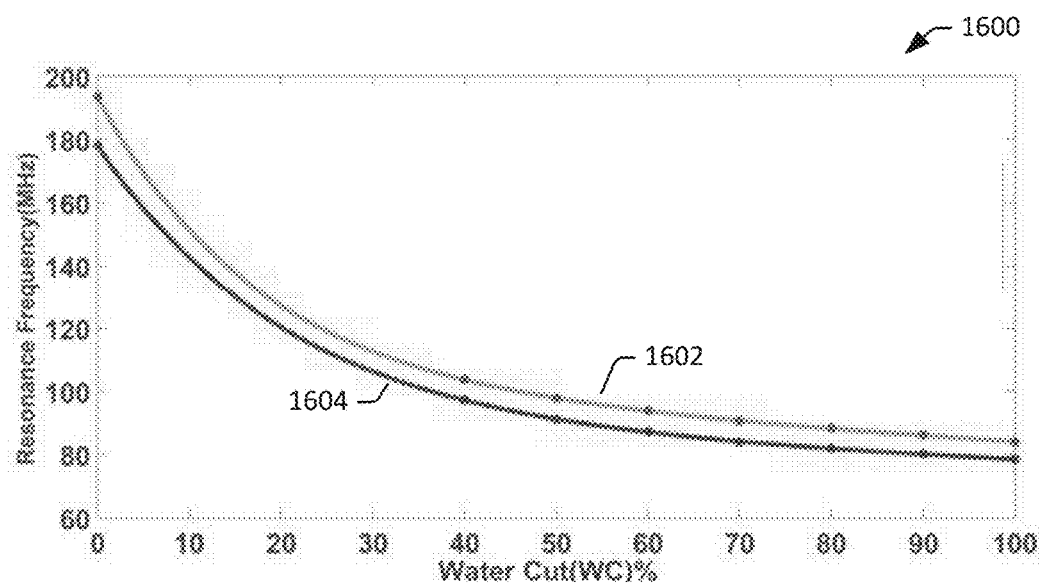
FIG. 16A is a plot diagram that illustrates an example comparison of simulated vs. measured characteristic curves of a WC sensor with homogeneously mixed oil and water in accordance with one or more embodiments.
Figure 16B:
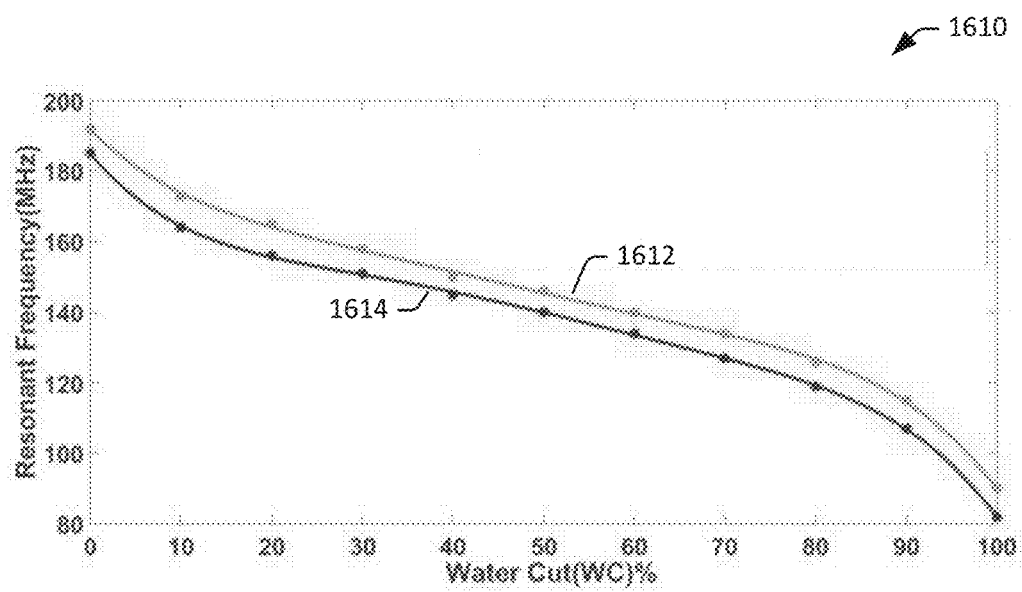
FIG. 16B is a plot diagram that illustrates an example comparison of simulated vs measured characteristic curves of a WC sensor with separate oil and water phases in accordance with one or more embodiments.

In some embodiments, as described below, in some embodiments, introducing the source signal at a signal conductor of a water-cut sensor disposed on a pipe having a fluid therein (block 1202) and/or sensing a response signal at the signal conductor (block 1204) may be conducted in a frequency sweep. For example, referring to the WC sensor 1102 of FIG. 10E, a vector network analyzer (VNA) of the measurement processing system 1106 may conduct a frequency sweep, supplying source signals having frequencies from about 50 MHz-130 Mhz to the input terminal 1150 of the feed line 1130 of the signal conductor 1110 of the water-cut sensor 1102 disposed on a pipe 104 and having the fluid 1108 therein. During the frequency sweep, the vector network analyzer (VNA) may measure the phase and frequency of corresponding response signals present at the output terminal 1152. The vector network analyzer (VNA) may assess these signals to determine a S21 response value for each of the frequencies. That is, a S21 response across the frequency range can be determined. FIG. 15 is a plot 1500 that illustrates example S21 responses of a water-cut sensor 1102 determined for fluids 1108 having a water-cut of about 100% to about 40% in accordance with one or more embodiments. For example, the first curve 1502, second curve 1504, third curve 1506, fourth curve 1508, fifth curve 1510, sixth curve 1512, and seventh curve 1514, represent example S21 responses determined for the water-cut sensor 102 with fluids having known water-cuts of 100%, 90%, 80%, 70%, 60%, 50% and 40%, respectively, present in the pipe 1104. The reliability of this technique has been verified through simulation and actual test results for fluids having known WC values. FIG. 16A is a plot 1600 that illustrates an example comparison of simulated vs measured characteristic curves of a WC of a fluid having homogeneously mixed oil and water in accordance with one or more embodiments. The top curve 1602 represent the characteristic curve based on actual measurements, and the bottom curve 1604 represents the characteristic curve based on simulated measurements. FIG. 16B is a plot 1610 that illustrates an example comparison of simulated vs measured characteristic curves of a WC of a fluid having separate oil and water phases in accordance with one or more embodiments. The top curve 1612 represent the characteristic curve based on actual measurements, and the bottom curve 1614 represents the characteristic curve based on simulated measurements.

In some embodiments, determining a resonance frequency of the signal conductor based at least in part on the response signal (block 1206) can include the measurement processing system 1106 determining a resonance frequency of the water-cut sensor with the fluid 1108 present in the pipe (e.g., the fluid 1108 present in the pipe 1104 when the source signal was introduced and/or the corresponding response signals were sensed). The resonance frequency may be identified, for example, as a well-defined dip the an S21 response across the relevant frequencies. Continuing with the above example, if a frequency sweep is conducted while a fluid 1108 having a WC of about 50% is flowing through the pipe 1104, the resulting S21 response curve may look similar to that of the sixth curve 1512, and the resonance frequency can be determined to about 91 MHz based on the well-defined dip in the S21 response (e.g., the frequency at about the lowest point on the S21 response curve 1512).

In some embodiments, determining a water-cut for the fluid mixture based at least in part on the determined resonance frequency (block 1208) can include the measurement processing system 1106 determining a WC that corresponds to the determined resonance frequency for the WC sensor 1102. For example, calibration test can be run with the a WC sensor 1102 (or a test WC sensor) in the same or similar conditions (e.g., on the pipe 1104, or a similar type/sized pipe) with fluids having different water-cuts to generate an equation, curve, look-up table or the like that represents water-cuts vs. observed resonance frequency. In response to determining the resonance frequency, the measurement processing system 1106 may employ this predefined relationship to determine the WC for the fluid 1108. For example, the measurement processing system 1106 may access a look-up-table to determine that fluid flowing through the pipe 1104 having an S21 response at about 91 MHz, has a water-cut of 50%. That is, if a frequency sweep indicates that the WC sensor 1102 has a dip (low point) in the S21 response at about 91 MHz, then it can be determined that the fluid 1108 in the pipe has a WC of about 50%.

In some embodiments, the above process can be performed continuously (e.g., in series, one after the other), on a regular basis (e.g., every minute, hourly, and/or the like), or the like so that the WC for a fluid 1108 flowing through the pipe 1104 can be continually or regularly determined. For example, the measurement processing system 1106 may initiate and conduct the operations of method 1200 continuously (e.g., in series, one after the other), on a regular basis (e.g., every minute, hourly, and/or the like), or the like, and the results may be presented (e.g., displayed to a well/production operator), stored in a memory (e.g., a WC log) for later review, and/or used for other related determinations.

In some embodiments, to manufacture a WC sensor for use in making WC measurements for fluid flowing through a pipe, some or all of the elements of a WC sensor can be formed directly onto the surface of the pipe. For example, one or more masks can be disposed about the surface of the pipe 1104 that provides one or more openings for the ground plane, the ground ring, the open shunt stub, and/or the feed line. A conductive paste can be disposed (e.g., sprayed, painted, and/or the like) into the opening(s) of the mask to form the ground plane, the ground ring, the open shunt stub, and/or the feed line. Once the conductive paste has cured, the corresponding mask portion can be removed, leaving a conductive pattern that includes the signal conductor and the ground conductor, formed from the cured conductive paste, disposed on the surface of the pipe.

Figure 13A:
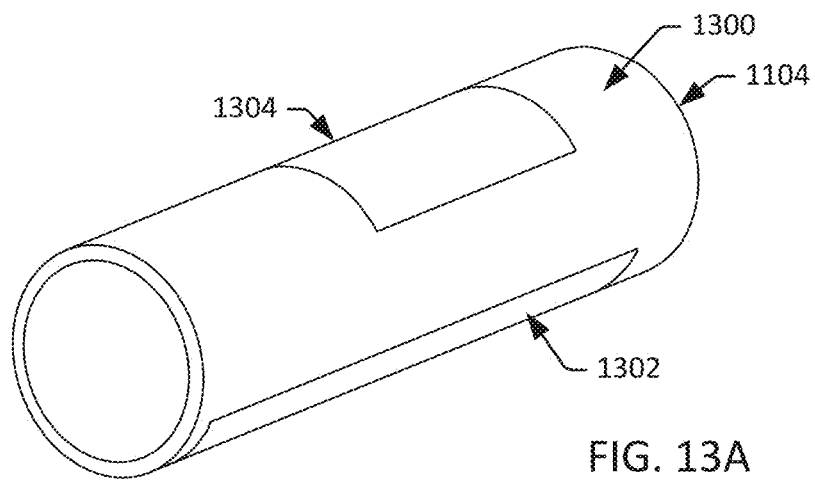
FIGS. 13A-13C are diagrams that illustrate examples of various masks that can be employed in the manufacture of a water-cut sensor in accordance with one or more embodiments.
Figure 13B:
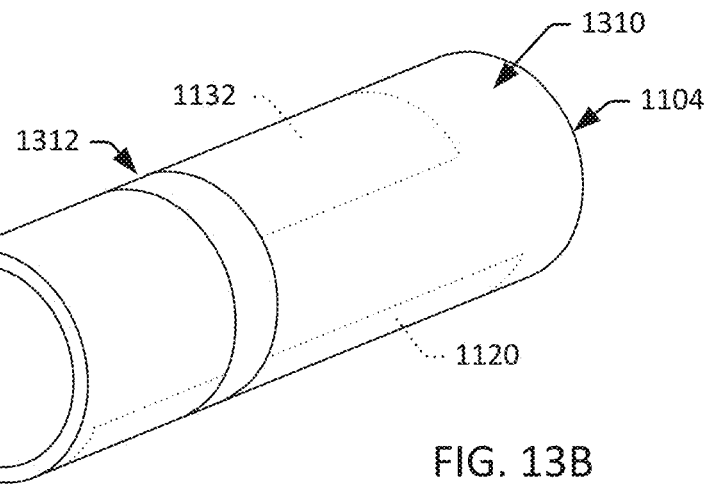
Figure 13C:
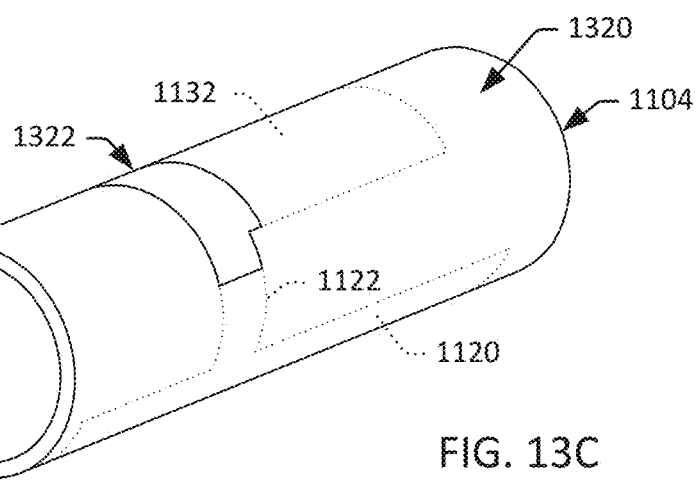

FIGS. 13A-13C are diagrams illustrating various masks that can be employed in the manufacture a WC sensor 1102 in accordance with one or more embodiments. FIG. 13A illustrates an example first mask 1300 in accordance with one or more embodiments. The first mask 1300 may include material covering some or all of the portions of the pipe 1104, other than in areas where openings in the first mask 1300 expose the surface of the pipe 1104 on which the ground plane 1120 and the open shunt stub 1112 (or at least a portion thereof) is to be disposed. That is, the first mask 1300 may provide a first opening 1302 for the ground plane 1120 and a second opening 1304 for at least a distal portion of the open shut stub 1132 (e.g., the portion distal from the ground ring 1122). FIG. 13B illustrates an example second mask 1310 in accordance with one or more embodiments. The second mask 1310 may include material covering some or all of the portions of the pipe 1104, other than in areas where opening(s) in the second mask 1310 expose the surface of the pipe 1104 and/or the ground plane 1120 on which the ground ring 1122 is to be disposed or at least attached. That is, the second mask 1310 may provide a third opening 1312 for the ground ring 1122. In some embodiments, the first mask 1300 may include the openings 1304, 1302 and 1312 such that the ground plane 1120, the open shunt stub 1132 and the ground ring 1122 can be formed at the same time (or at least using the single mask 1300). FIG. 13C illustrates an example third mask 1320 in accordance with one or more embodiments. The third mask 1320 may include material covering some or all of the portions of the pipe 104, other than in areas where opening(s) in the third mask 1320 expose the surface of the pipe 104, the ground ring 1122 and/or the dielectric separator 1140 on which on which the feed line 1130 and/or the proximal portion of the open shunt stub 1132 is to be disposed. That is, the third mask 1320 may provide a fourth opening 1322 for the feed line 1130 and/or the proximal portion of the open shunt stub 1132.

Figure 14:
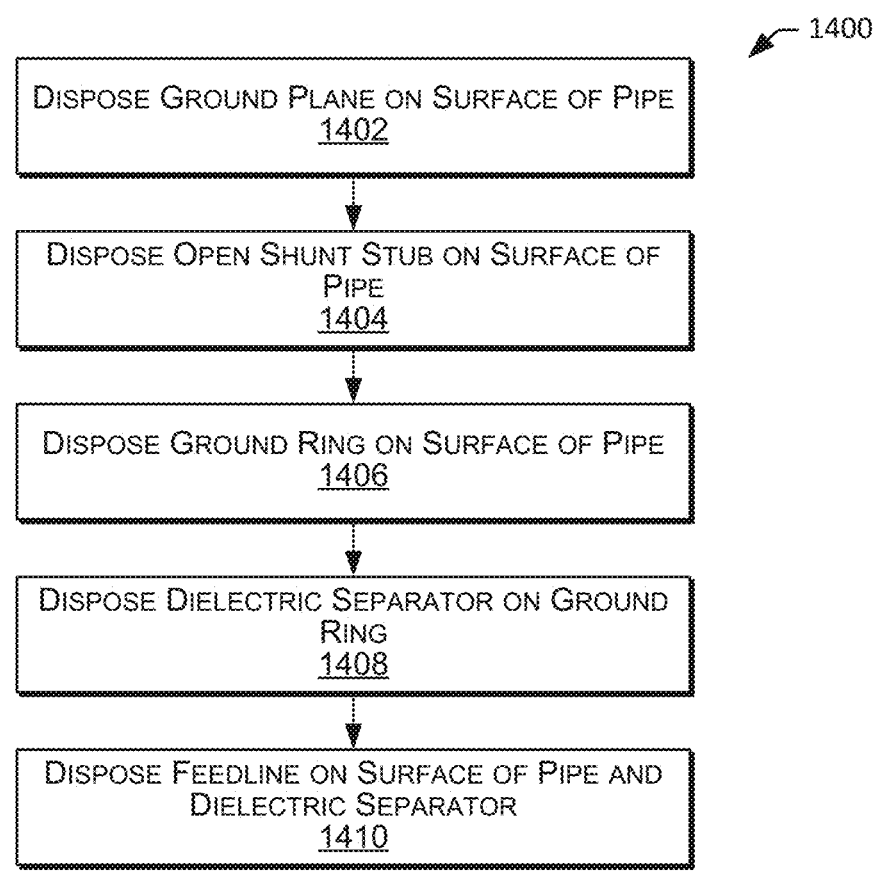
FIG. 14 is a flowchart that illustrates an example method of manufacturing a microwave based water-cut sensor for a pipe in accordance with one or more embodiments.

FIG. 14 is a flowchart that illustrates a method 1400 of manufacturing a microwave based water-cut sensor for a pipe in accordance with one or more embodiments. Method 1400 may generally include disposing the ground plane on the surface of the pipe (block 1402), disposing the open shunt stub on the surface of the pipe (block 1404), disposing the ground ring on the surface of the pipe (block 1406), disposing the dielectric separator on ground ring (block 1408), and disposing the feed line on the surface of the pipe (block 1410).

In some embodiments, disposing the ground plane on the surface of the pipe (block 1402) and disposing the open shunt stub on the surface of the pipe (block 1404) can include disposing the first mask 1300 on the surface of the pipe 1104, and disposing (e.g., spraying, painting, and/or the like) a conductive material (e.g., a copper based paste) into the first opening 1302 (e.g., to form the ground plane 1120) and the second opening 1304 (e.g., to form at least a distal portion of the open shut stub 1132) (e.g., the open shut stub 1132 distal from the ground ring 1122). The first mask 1300 may be removed, for example, once the conductive paste has cured.

In some embodiments, disposing the ground ring on the surface of the pipe (block 1406) can include disposing the second mask 1310 on the surface of the pipe 104, and disposing (e.g., spraying, painting, and/or the like) a conductive material (e.g., a copper based paste) into the third opening 1312 (e.g., to form the ground ring 1122). The conductive material may be disposed on the exposed surface of the pipe 1104 and/or over the ground plane 1120. The second mask 1310 may be removed, for example, once the conductive paste has cured. In some embodiments, the first mask 1300 may include the openings 1304, 1302 and 1312 such that the ground plane 1120, the open shunt stub 1132 and the ground ring 1122 can be formed at the same time (or at least using the single mask).

In some embodiments, disposing the dielectric separator on ground ring (block 1408) can include obtaining dielectric separator 1140 (e.g., a strip of dielectric material, such as a piece of Teflon tape) that is about the size of the feed line 1130 to be formed, and placing the dielectric separator 1140 on the exterior surface of the ground ring 1122 that is to be overlapped by the feed line 1130.

In some embodiments, disposing the feed line on the surface of the pipe (block 1410) can include disposing the third mask 1320 on the surface of the pipe 104 (and over the dielectric separator 1140), and disposing (e.g., spraying, painting, and/or the like) a conductive material (e.g., a copper based paste) into the fourth opening 1322 (e.g., to form the feed line 1130 and/or the proximal portion of the open shunt stub 1132). The third mask 1320 may be removed, for example, once the conductive paste has cured. In some embodiments, an input and/or and output port may be provided. For example, a terminal (e.g., an SubMiniature version A (SMA) connector) for the input port 1150 may be provided at a first end of the feed line 1130 and a terminal (e.g., an SMA connector) for the output port 1152 may be provided at a second end of the feed line 1130 (e.g., opposite the first end of the feed line 1130).

In some embodiments, the measurement processing system 106 (or 1106) can include a computer system (e.g., computer system 2000, described below) for performing some or all of the operations described with regard to the measurement processing system 106 (or 1106). For example, measurement processing system 106 (or 1106) may include a computer for automatically controlling an external device (e.g., vector network analyzer (VNA) of the measurement processing system 106 (or 1106)) to conduct one or more frequency sweeps across the WC sensor 102 (or 1102) on the pipe 104 (or 1104), and to process the corresponding signals to determine a WC measurements for the fluid 108 (or 1108) flowing through the pipe 104 (or 1104).

Figure 17:
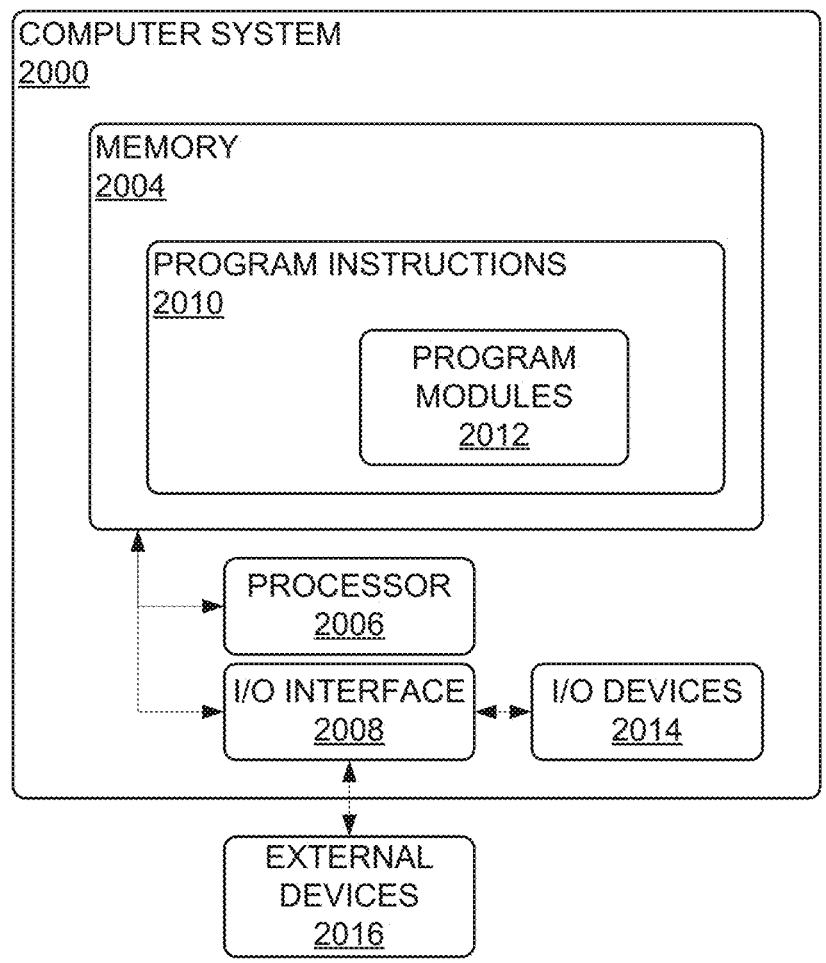
FIG. 17 is a diagram that illustrates an example computer system in accordance with one or more embodiments.

FIG. 17 is a diagram that illustrates an example computer system 2000 in accordance with one or more embodiments. In some embodiments, the computer system 2000 may include a memory 2004, a processor 2006, and an input/output (I/O) interface 2008. The memory 2004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 2004 may include a non-transitory computer-readable storage medium having program instructions 2010 stored therein. The program instructions 2010 may include program modules 2012 that are executable by a computer processor (e.g., the processor 2006) to cause the functional operations described herein, including those described with regard to the processes described herein, including the methods 1200 and 1400. In the context of a computer system of a measurement processing system 106 (or 1106), the program modules 2012 may include one or more user modules for performing some or all of the operations described with regard to the measurement processing system 106 (or 1106).

The processor 2006 may be any suitable processor capable of executing/performing program instructions. The processor 2006 may include a central processing unit (CPU) that carries out program instructions (e.g., the program instructions of the program module(s) 2012) to perform the arithmetical, logical, and input/output operations described herein. The processor 2006 may include one or more processors. The I/O interface 2008 may provide an interface for communication with one or more I/O devices 2014, such as a joystick, a computer mouse, a keyboard, a display screen (e.g., an electronic display for displaying a graphical user interface (GUI)), and/or the like. The I/O devices 2014 may include one or more of the user input devices. The I/O devices 2014 may be connected to the I/O interface 2008 via a wired or a wireless connection. The I/O interface 2008 may provide an interface for communication with one or more external devices 2016, such as other computers, networks, and/or the like. In some embodiments, the I/O interface 2008 may include an antenna, a transceiver, and/or the like. In some embodiments, the computer system 200 and/or the external devices 2016 may include a vector network analyzer (VNA). Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A water-cut sensor system comprising:
   a cylindrical pipe for routing the flow of a production fluid comprising a mixture of oil and water;
   a microwave resonator water-cut sensor comprising:
      a T-resonator disposed on a first side of a cylindrical pipe, the T resonator comprising:
         a feed line comprising a conductive material disposed about a first portion of an external surface of the cylindrical pipe extending in a circumferential direction about the cylindrical pipe;
         an open shunt stub comprising a conductive material disposed on a second portion of the external surface of the cylindrical pipe extending in a longitudinal direction along the cylindrical pipe, the open shunt stub being conductively coupled to the feed line;
         an input terminal located at a first end of the feed line; and
         an output terminal located at a second end of the feed line;
      a ground conductor disposed on a second side of the cylindrical pipe that is opposite the first side, the ground conductor comprising:
         a ground plane comprising a conductive material disposed on a third portion of the external surface of the cylindrical pipe extending in the longitudinal direction along the cylindrical pipe, wherein the third portion of the external surface of the pipe is opposite the second portion of the external surface of the pipe such that the open shunt stub is disposed on the first side of the cylindrical pipe and the ground plane is disposed on the second side of the cylindrical pipe that is opposite the first side; and
         a ground ring comprising a conductive material disposed on a fourth portion of the external surface of the cylindrical pipe extending in a circumferential direction about the pipe, the ground ring being conductively coupled to the ground plane, and the first portion overlapping the fourth portion such that the feed line overlaps the ground ring; and
      a separator comprising a dielectric material disposed between the feed line and the portion of the ground ring overlapped by the feed line, the separator being configured to electrically isolate the T-resonator from the ground conductor; and
   a measurement system configured to:
      introduce, to the feed line of the T-resonator via the input terminal, source signals of different frequencies;
      sense, from the feed line of the T-resonator via the output terminal, response signals corresponding to the source signals;
      determine a resonance frequency of the microwave resonator water-cut sensor based at least in part on the source signals and the response signals; and
      determine a percentage of oil or water in the fluid based at least in part on the resonance frequency of the microwave resonator water-cut sensor.

2. The system of claim 1, wherein the open shunt stub has a length that is the same or greater than a diameter of the cylindrical pipe.

3. The system of claim 1, wherein the open shunt stub has a length that is between three and five times the diameter of the cylindrical pipe.

4. The system of claim 1, wherein the feed line has a length that is the same or greater than a width of the shunt stub.

5. The system of claim 1, wherein the ground ring has a width that is the same or greater than a width of the feed line.

6. The system of claim 1, wherein the separator has a width that is the same or greater than a width of the feed line, and a length that is the same or greater than a length of the feed line.

7. The system of claim 1, wherein the ground plane has a width determined based on an average of a first width associated with a minimum resonance frequency for oil and a second width associated with a minimum resonance frequency for water.

8. The system of claim 1, wherein determining a resonance frequency of the microwave resonator water-cut sensor based at least in part on the source signals and the response signals comprises determining a frequency corresponding to a low point of a S21 response determined based on the source signals and the response signals.

9. The system of claim 1, wherein introducing source signals of one or more frequencies comprises conducting a frequency sweep across an operating range for the microwave resonator water-cut sensor.

10. A water-cut sensor system comprising:
a T-resonator comprising:
a feed line comprising a conductive material disposed about a first portion of an external surface of a pipe extending in a circumferential direction about the pipe; and
an open shunt stub comprising a conductive material disposed on a second portion of the external surface of the pipe extending in a longitudinal direction along the pipe, the open shunt stub being conductively coupled to the feed line;
a ground conductor comprising:
a ground plane comprising a conductive material disposed on a third portion of the external surface of the cylindrical pipe extending in the longitudinal direction along the cylindrical pipe, wherein the third portion of the external surface of the pipe is opposite the second portion of the external surface of the pipe; and
a ground ring comprising a conductive material disposed on a fourth portion of the external surface of the cylindrical pipe extending in a circumferential direction about the pipe, the ground ring being conductively coupled to the ground plane, and the first portion overlapping the fourth portion such that the feed line overlaps the ground ring; and
a separator comprising a dielectric material disposed between the feed line and the portion of the ground ring overlapped by the feed line, the separator being configured to electrically isolate the T-resonator from the ground conductor.

11. The system of claim 10, wherein the open shunt stub has a length that is the same or greater than a diameter of the pipe.

12. The system of claim 10, wherein the open shunt stub has a length that is between three and five times the diameter of the pipe.

13. The system of claim 10, wherein the feed line has a length that is the same or greater than a width of the shunt stub.

14. The system of claim 10, wherein the ground ring has a width that is the same or greater than a width of the feed line.

15. The system of claim 10, wherein the separator has a width that is the same or greater than a width of the feed line, and a length that is the same or greater than a length of the feed line.

16. The system of claim 10, wherein the ground plane has a width determined based on an average of a first width associated with a minimum resonance frequency for oil and a second width associated with a minimum resonance frequency for water.

17. The system of claim 10, wherein the pipe is a cylindrical pipe, and wherein the T-resonator is disposed on a first side of the pipe, and the ground conductor is disposed on a second side of the pipe that is opposite the first side of the pipe.

18. The system of claim 10, wherein the T-resonator comprises:
an input terminal located at a first end of the feed line, wherein the input terminal is configured to receive source signals from an external circuit; and
an output terminal located at a second end of the feed line, wherein the output terminal is configured to provide for sensing, by an external circuit, of response signals corresponding to the source signals, and
wherein a resonance frequency of the microwave resonator water-cut sensor is determined based at least in part on the source signals and the response signals, and
a water-cut of fluid in the cylindrical pipe is determined based at least in part on the resonance frequency of the microwave resonator water-cut sensor.

19. The system of claim 10, further comprising a measurement system configured to:
introduce, to the feed line of the T-resonator, source signals of different frequencies;
sense, from the feed line of the T-resonator, response signals corresponding to the source signals;
determine a resonance frequency based at least in part on the source signals and the response signals; and
determine a water-cut of a fluid in the pipe based at least in part on the resonance frequency of the microwave resonator water-cut sensor.

20. The system of claim 19, wherein determining a resonance frequency based at least in part on the source signals and the response signals comprises determining a frequency corresponding to a low point of an S21 response determined based on the source signals and the response signals.

21. The system of claim 19, wherein introducing source signals of one or more frequencies comprises conducting a frequency sweep across an operating range for the water-cut sensor.

22. A method for sensing water-cut of a fluid in a cylindrical pipe, the method comprising:
introducing, to a T-resonator of a water-cut sensor disposed on the cylindrical pipe, source signals of different frequencies, wherein the water-cut sensor comprises:
the T-resonator comprising:
a feed line comprising a conductive material disposed about a first portion of an external surface of the pipe extending in a circumferential direction about the pipe; and
an open shunt stub comprising a conductive material disposed on a second portion of the external surface of the pipe extending in a longitudinal direction along the pipe, the open shunt stub being conductively coupled to the feed line;

a ground conductor comprising:
- a ground plane comprising a conductive material disposed on a third portion of the external surface of the cylindrical pipe extending in the longitudinal direction along the cylindrical pipe, wherein the third portion of the external surface of the pipe is opposite the second portion of the external surface of the pipe; and
- a ground ring comprising a conductive material disposed on a fourth portion of the external surface of the cylindrical pipe extending in a circumferential direction about the pipe, the ground ring being conductively coupled to the ground plane, and the first portion overlapping the fourth portion such that the feed line overlaps the ground ring; and
- a separator comprising a dielectric material disposed between the feed line and the portion of the ground ring overlapped by the feed line, the separator being configured to electrically isolate the T-resonator from the ground conductor;

sensing, from the T-resonator of the water-cut sensor, response signals corresponding to the source signals;

determining a resonance frequency of the water-cut sensor based at least in part on the source signals and the response signals; and determining a percentage of oil or water in the fluid based at least in part on the resonance frequency of the water-cut sensor.

23. A method for manufacturing a water-cut sensor, the method comprising:
- disposing a first mask on an external surface of the pipe, the first mask comprising a first opening at a first portion of the external surface of the pipe for forming an open shunt stub of a T-resonator;
- disposing a conductive material into the first opening to form the open shunt stub of the T-resonator on the first portion of the external surface of the pipe;
- disposing a second mask on the external surface of the pipe, the second mask comprising a second opening at a second portion of the external surface of the pipe for forming a ground plane of a ground conductor, the second portion of the external surface being opposite the first portion of the external surface;
- disposing a conductive material into the second opening to form the ground plane of the ground conductor on the second portion of the external surface of the pipe;
- disposing a third mask on an external surface of the pipe, the third mask comprising a third opening at a third portion of the external surface of the pipe for forming a ground ring of the ground conductor, the third portion extending at least from the ground plane about a circumference of the pipe;
- disposing a conductive material into the third opening to form the ground ring of the ground conductor on the third portion of the external surface of the pipe, the ground ring being conductively coupled to the ground plane;
- disposing a dielectric separator on at least a portion of the ground ring to be overlapped by a feed line of the T-resonator;
- disposing a fourth mask on an external surface of the pipe, the fourth mask comprising a fourth opening at an external surface of the dielectric separator for forming the feed line of the T-resonator; and
- disposing a conductive material into the fourth opening to form the feed line of the T-resonator on the external surface of the dielectric separator, the feed line being conductively coupled to the open shunt stub.

* * * * *